United States Patent
Goldstein et al.

(10) Patent No.: US 9,715,562 B2
(45) Date of Patent: Jul. 25, 2017

(54) METHODS AND SYSTEMS FOR EAR DEVICE DESIGN USING COMPUTERIZED TOMOGRAPHY (CT)-COLLECTED ANTHROPOMORPHIC DATA

(71) Applicant: Personics Holdings, LLC, Boca Raton, FL (US)

(72) Inventors: Steven W. Goldstein, Delray Beach, FL (US); Sergei Azernikov, Irvine, CA (US)

(73) Assignee: Personics Holdings, LLC, Boca Raton, FL (US)

( * ) Notice: Subject to any disclaimer, the term of this patent is extended or adjusted under 35 U.S.C. 154(b) by 652 days.

(21) Appl. No.: 14/362,603

(22) PCT Filed: Dec. 6, 2012

(86) PCT No.: PCT/US2012/068143
§ 371 (c)(1),
(2) Date: Jun. 4, 2014

(87) PCT Pub. No.: WO2013/086116
PCT Pub. Date: Jun. 13, 2013

(65) Prior Publication Data
US 2014/0343900 A1    Nov. 20, 2014

Related U.S. Application Data

(60) Provisional application No. 61/567,141, filed on Dec. 6, 2011.

(51) Int. Cl.
| | |
|---|---|
| *G06F 17/50* | (2006.01) |
| *A61B 6/03* | (2006.01) |
| *G02C 13/00* | (2006.01) |
| *H04R 1/10* | (2006.01) |
| *H04R 25/00* | (2006.01) |
| *G06F 17/18* | (2006.01) |
| *G06T 3/00* | (2006.01) |
| *G06T 17/00* | (2006.01) |

(Continued)

(52) U.S. Cl.
CPC ............. *G06F 17/50* (2013.01); *A61B 6/032* (2013.01); *G02C 13/003* (2013.01); *G06F 17/18* (2013.01);
(Continued)

(58) Field of Classification Search
USPC .................................................... 703/1, 2, 6
See application file for complete search history.

(56) References Cited

U.S. PATENT DOCUMENTS 8,014,870 B2 * 9/2011 Seidman ................ A61N 1/361
                                                                    600/411
2003/0223083 A1    12/2003 Geng
(Continued)

OTHER PUBLICATIONS

WIPO, PCT International Search Report and Written Opinion for International Application No. PCT/12/68143, Dated Feb. 15, 2013, 9 pages.

*Primary Examiner* — Thai Phan
(74) *Attorney, Agent, or Firm* — Pablo Meles

(57) ABSTRACT

Methods and systems for designing an earpiece device are provided. The method includes receiving a plurality of images for a respective plurality of individuals. Each image includes at least one ear anatomy. For each image, a three-dimensional (3D) surface representing the at least one ear anatomy is extracted, to form a plurality of extracted surfaces corresponding to the plurality of images. At least one statistical measurement representative of at least a portion of the plurality of individuals is determined from among the plurality of extracted surfaces. At least one design parameter for the earpiece device is optimized based on the at least one statistical measurement, The earpiece device is formed using the optimized at least one design parameter.

34 Claims, 20 Drawing Sheets

(51) Int. Cl.
    *G06T 7/35*         (2017.01)
    *A61B 6/00*        (2006.01)
    *A61B 8/08*        (2006.01)
    *A61B 5/055*      (2006.01)
    *A61B 5/12*        (2006.01)

(52) U.S. Cl.
    CPC .............. G06T 3/0068 (2013.01); G06T 7/35 (2017.01); G06T 17/00 (2013.01); H04R 1/1058 (2013.01); H04R 25/658 (2013.01); *A61B 5/055* (2013.01); *A61B 5/12* (2013.01); *A61B 6/469* (2013.01); *A61B 6/5217* (2013.01); *A61B 8/5223* (2013.01); *G06T 2200/04* (2013.01); *G06T 2207/10081* (2013.01); *G06T 2207/30052* (2013.01); *H04R 2201/029* (2013.01); *H04R 2225/77* (2013.01)

(56) References Cited

U.S. PATENT DOCUMENTS

| | | | |
|---|---|---|---|
| 2004/0107080 A1* | 6/2004 | Deichmann | A61F 11/08 703/6 |
| 2010/0081926 A1* | 4/2010 | Hyde | A61B 5/0084 600/431 |
| 2010/0081928 A1* | 4/2010 | Hyde | A61B 5/0084 600/431 |
| 2010/0318208 A1 | 12/2010 | Schiller et al. | |

* cited by examiner

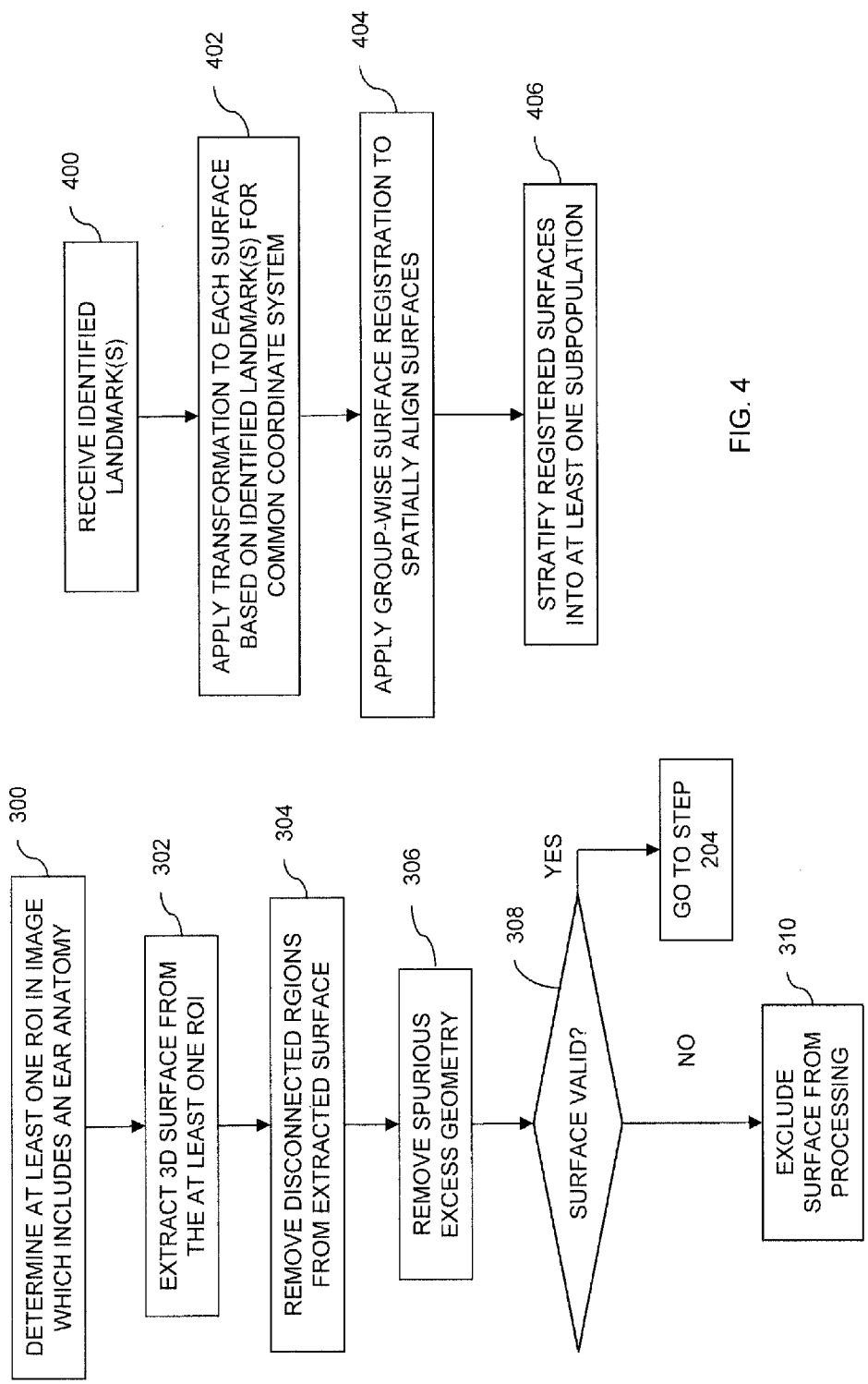

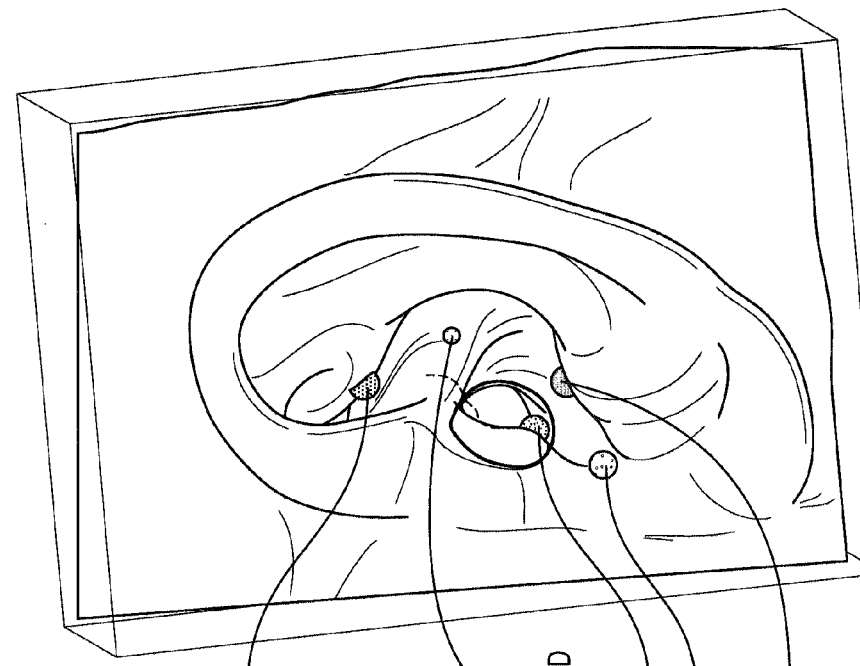
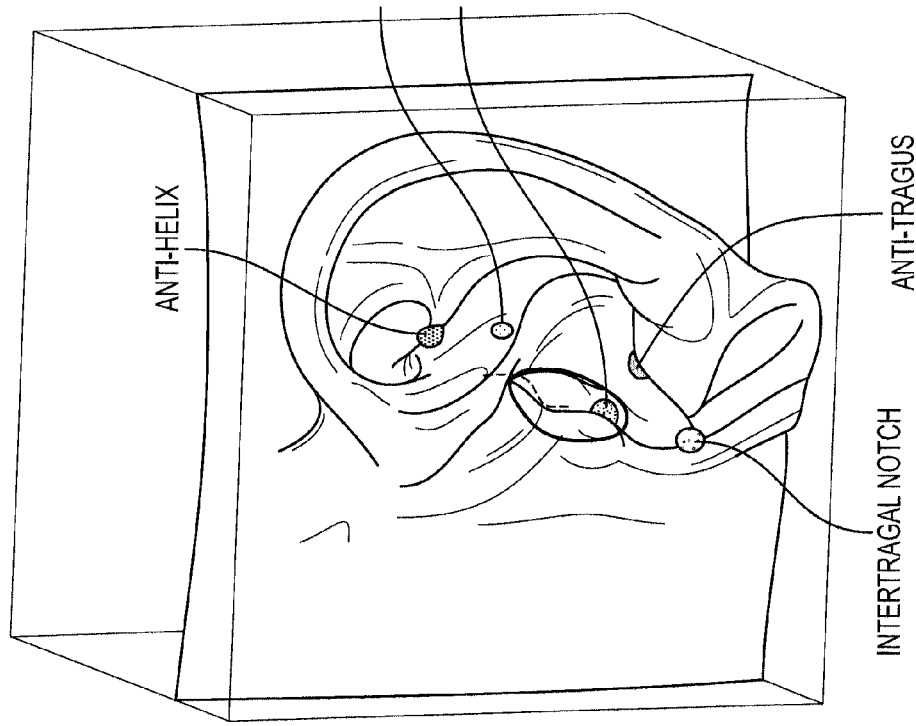
FIG. 9B
FIG. 9A

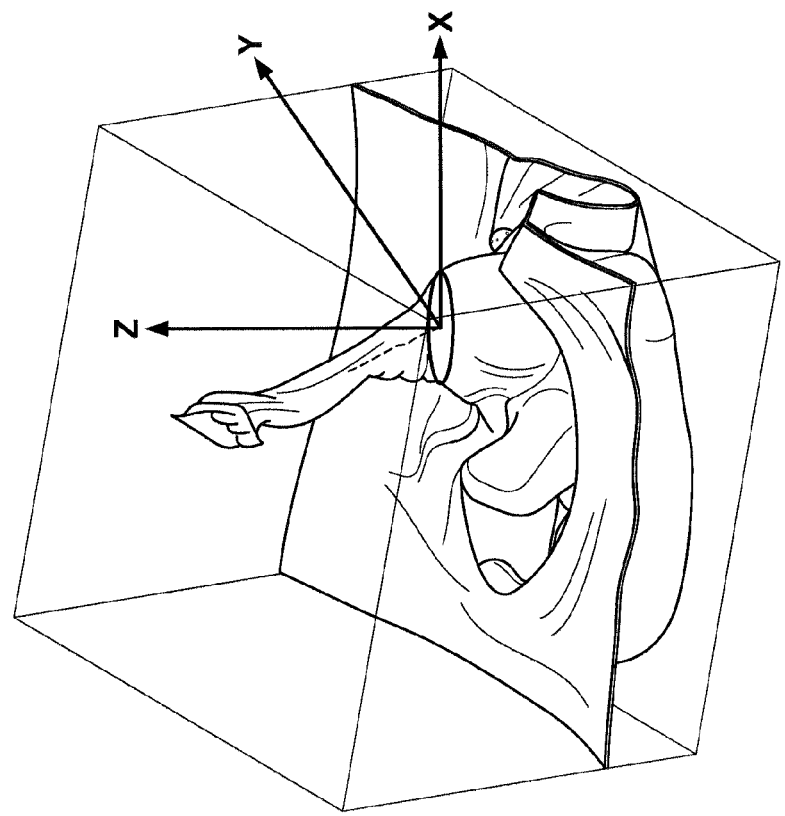
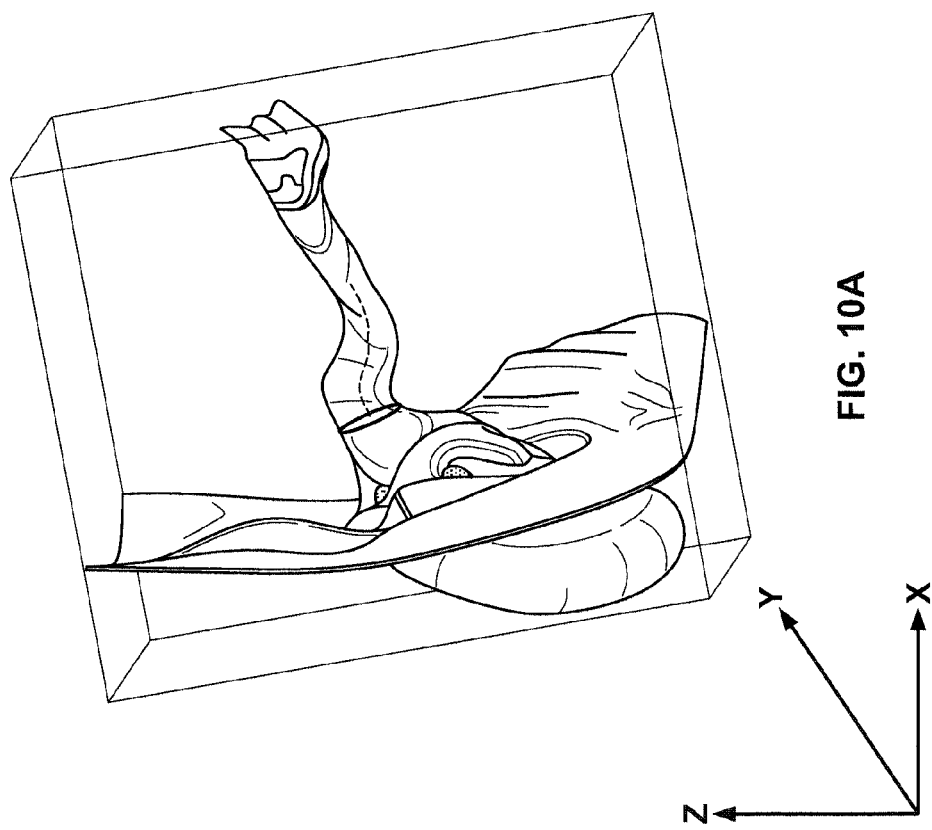

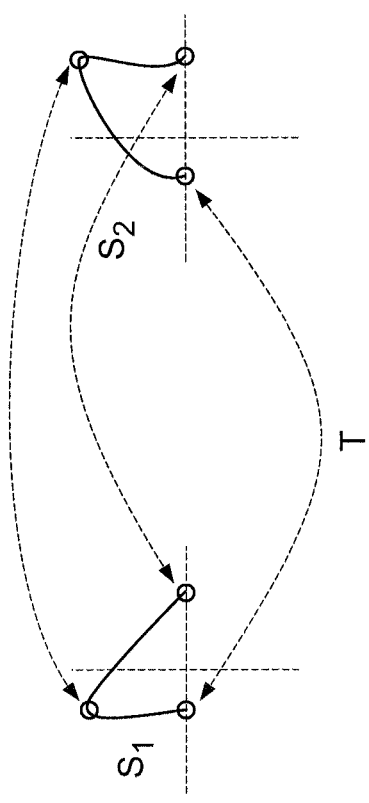
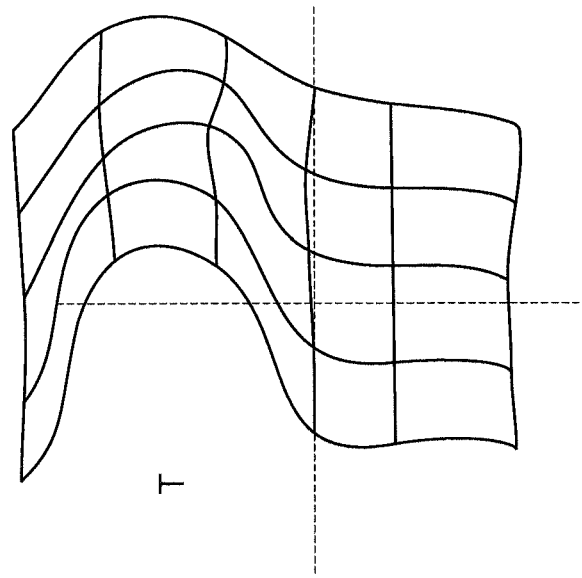
FIG. 11B
FIG. 11A

METHODS AND SYSTEMS FOR EAR DEVICE DESIGN USING COMPUTERIZED TOMOGRAPHY (CT)-COLLECTED ANTHROPOMORPHIC DATA

CROSS REFERENCE TO RELATED APPLICATIONS

This application is a 371 National Stage Entry from PCT Application No. PCT/US2012/068143 entitled "METHODS AND SYSTEMS FOR EAR DEVICE DESIGN USING COMPUTERIZED TOMOGRAPHY (CT)-COLLECTED ANTRHOPOMORPHIC DATA," filed 6 Dec. 2012, incorporated fully herein by reference. This application claims priority to U.S. Provisional Application Ser. No. 61/567,141 entitled "METHODS AND SYSTEMS FOR EAR DEVICE DESIGN USING COMPUTERIZED TOMOGRAPHY (CT)-COLLECTED ANTRHOPOMORPHIC DATA," filed Dec. 6, 2011, incorporated fully herein by reference.

FIELD OF THE INVENTION

The present invention relates to the field of earpiece device design and, more particularly, to methods and systems for designing earpiece devices using at least one statistical measurement representative of at least a portion of a population based on images for the population which include ear anatomies.

BACKGROUND OF THE INVENTION

Ergonomics is a fundamental part of product design, particularly for devices that are in physical contact with the user for long periods of time, such as, but not limited to, in-ear devices including earphones, hearing aids, and ear plugs. Comfort may be an important factor regarding a product's success. Product comfort may be achieved through a precise fitting of the device in the user's external auditory canal (EAC) and concha. However, it is well known that there is a large degree of morphological variation across individuals, particularly in the EAC, concha, pinna and pinna distance to the skull. Furthermore, there is a lack of comprehensive anthropometric studies available in the literature relevant to the design of products in this category.

SUMMARY OF THE INVENTION

The present invention is embodied in a method of designing an earpiece device. The method includes receiving a plurality of images for a respective plurality of individuals, where each image includes at least one ear anatomy. For each image, a three-dimensional (3D) surface is extracted which represents the at least one ear anatomy, forming a plurality of extracted surfaces corresponding to the plurality of images. At least one statistical measurement representative of at least a portion of the plurality of individuals is determined from among the plurality of extracted surfaces. At least one design parameter for the earpiece device is optimized based on the at least one statistical measurement. The earpiece device is formed using the optimized at least one design parameter.

The present invention is further embodied in a system for designing an earpiece device. The system includes a surface extractor and a statistical measurement unit. The surface extractor is configured to receive a plurality of images for a respective plurality of individuals. Each image includes at least one ear anatomy. The surface extractor is configured to extract, for each image, a 3D surface representing the at least one ear anatomy, to form a plurality of extracted surfaces corresponding to the plurality of images. The statistical measurement unit is configured to determine at least one statistical measurement representative of at least a portion of the plurality of individuals from among the plurality of extracted surfaces and optimize at least one design parameter for the earpiece device based on the at least one statistical measurement. The earpiece device is designed using the optimized at least one design parameter.

Aspects of the present invention relate to a design process and system to optimize an earpiece device fit for a specific population such as an age, an ethnicity, etc. By optimizing the fit, the earpiece device may, for example, be worn for longer lengths of time (i.e., a wearability), may offer improved acoustical properties and may offer enhanced human factor handling.

BRIEF DESCRIPTION OF THE DRAWINGS

The invention may be understood from the following detailed description when read in connection with the accompanying drawing. It is emphasized that, according to common practice, various features of the drawing may not be drawn to scale. On the contrary, the dimensions of the various features may be arbitrarily expanded or reduced for clarity. Moreover, in the drawing, common numerical references are used to represent like features. Included in the drawing are the following figures:

FIG. 3 is a flow chart diagram illustrating an exemplary method for extracting a surface from an image, according to an aspect of the present invention;

FIG. 4 is a flow chart diagram illustrating an exemplary method for applying group-wise registration to a plurality of extracted surfaces, according to an aspect of the present invention;

FIGS. 9A and 9B are 3D images of example left ear surfaces of different individuals illustrating detected landmarks, according to an aspect of the present invention;

FIGS. 10A and 10B are 3D images of example three-dimensional (3D) surfaces before and after translation into a common coordinate system, according to an aspect of the present invention;

FIGS. 11A and 11B are illustrations of an example surface registration process for two surfaces, according to an aspect of the present invention;

DETAILED DESCRIPTION OF THE INVENTION

Figure 1:
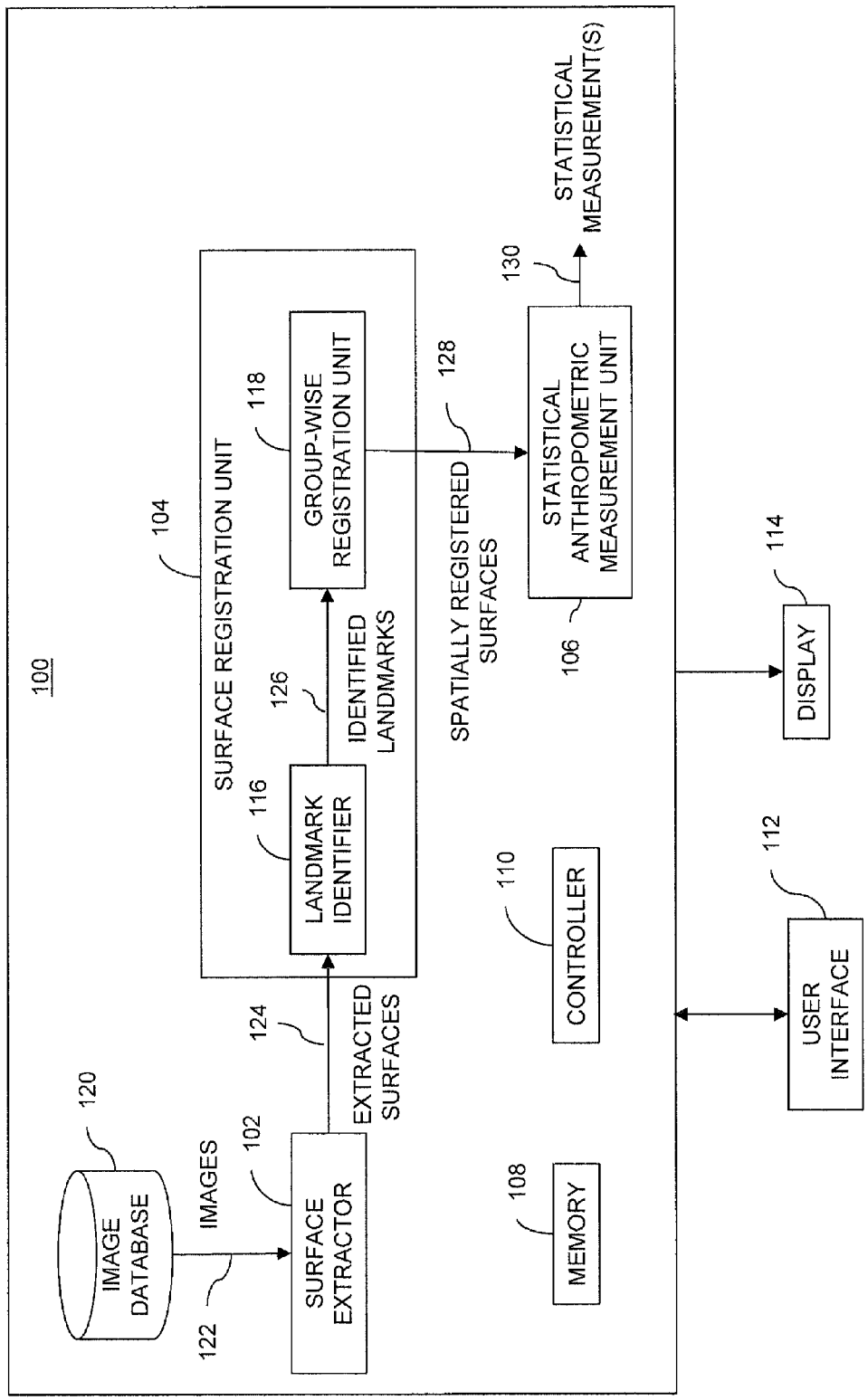
FIG. 1 is a functional block diagram of an exemplary anthropometric measurement system, according to an aspect of the present invention.

In addition to comfort, fit, stability, occlusion characteristics and acoustic properties of an earpiece device may also be important factors regarding a product's success. A relationship between all of these characteristics are often in conflict. As an example, for in-canal earpiece devices, it is typically very challenging to obtain comfort, of a goal of the earpiece device is to produce a high level of occlusion (attenuation).

As discussed above, there is a large degree of morphological variation across individuals, as well as a lack of available comprehensive anthropometric studies. Although there are a number of databases available which contain EAC data, the data is typically acquired by making an impression (e.g., by placing malleable material into regions of the ear) of an ear canal. Once the impression material cures, a process is used to acquire the "positive" image by a 3D scanning technique. This conventional method may yield satisfactory replica performance when the earpiece device is intended for use in the EAC. Unfortunately, during the impression acquisition process, typically only a small portion of the concha is captured, and the pinna is almost never captured.

The inventors have determined that, when developing a quality earpiece device design, it is desirable to base the design on a comprehensive set of variables including, for example, without being limited to, an orifice at the EAC, a concha bowl volume, a concha length, a concha height, a tragus thickness, an antitragus location, antitragus dimensions, an EAC diameter, an EAC volume, an EAC length, a first bend location, a second bend location, a pinna, a helix, a crus of helix and an antihelix. According to an exemplary embodiment, all of these anthropomorphic variables may be considered for an earpiece device design. In order to consider all of these variable, a complete ear anatomy is captured capturing the complete ear (i.e., the entire ear anatomy including the pinna, the concha, the EAC and the eardrum (also referred to herein as the tympanic membrane) in situ. Accordingly, aspects of the invention may consider the interconnected relationship between the pinna, concha and EAC (as opposed to relying upon static information such as EAC measurements), and how they function together as an anatomical system. It is understood that the present invention is not limited to acquiring all of the anthropomorphic variables described above or to obtaining a complete ear anatomy. According to another exemplary embodiment, one or more anthropomorphic variables may be acquired for at least one of the pinna, the concha or the EAC.

Another challenge for high quality product design is the potential for different ear anthropometry for various subpopulations. For example, women tend to have smaller ear anatomy than men (for example, with respect to concha length and width). However, there exists little useful information related to other stratifications of the population (i.e., subpopulations), such as those based on ethnicity, weight, and age. Accordingly, it may be desirable to determine to what degree the ear anthropometry varies for these subpopulations, and if a "one size fits all" approach is suitable for the design of in-ear devices.

Aspects of the present invention include an automated digital anthropometric measurement system (ADAMS) to support size and shape-related queries useful for product design. According to an exemplary embodiment, the system may provide stratification of the data for subpopulation analyses, as well as statistical measurements for at least one subpopulation and/or the population. In addition to average measurements, the system may determine variation about the mean using statistical descriptors such as the 95% confidence interval. In the description below, an exemplary system is described with respect to an ear anatomy, including structures such as the EAC, concha and pinna. It is understood, however, that the ear-based system is an exemplary embodiment, and that the system may be used for other parts of the anatomy including, without being limited to, the eyes (e.g., for eyewear design), the feet (e.g., for shoe design) or the head (e.g., for helmet design).

Aspects of the present invention relate to methods and systems for designing an earpiece device. An exemplary method includes receiving a plurality of images for a respective plurality of individuals, where each image including at least one ear anatomy. For each image, a three-dimensional (3D) surface representing the at least one ear anatomy may be extracted, to form a plurality of extracted surfaces corresponding to the plurality of images. At least one statistical measurement representative of at least a portion of the plurality of individuals may be determined from among the plurality of extracted surfaces. At least one design parameter for the earpiece device may be optimized based on the at least one statistical measurement, and the earpiece device may be formed using the optimized at least one design parameter.

In an exemplary embodiment, acquisition of human anthropomorphic data is obtained through Computerized Tomography (CT). The CT modality may be used to acquire anatomical data for physical measurements outside the cavity of the human body. CT is normally utilized for diagnostic imaging of: organs, bones, and tissue. CT is a medical imaging method employing tomography created by computer processing. Digital geometry processing may be used to generate a three-dimensional image of the inside of an object from a large series of two-dimensional X-ray images taken around a single axis of rotation.

CT studies may be used to create a compendium of human ear anthropomorphics from the eardrum to the pinna. These findings may be used to aid in earphone, earplug or other appliance (designated generally as an earpiece device) that is inserted into the concha and or EAC to be comfortable, stable, reduce cerumen production within human ears and to fit in such a way as to produce the acoustical benefits necessary for the earpiece device to operate effectively.

The collection and analysis of anthropomorphic data may be used in the development of an earpiece device, which may need to fit a large geographic distribution subject base. Demographic information (such as gender, age, weight, ethnicity and race) may have some bearing on the anthropomorphics of the ear. These variables may be compared to determine any patterns among various subpopulations. Furthermore, other anthropomorphic information such as foot size, hat size, neck size, thumb size, ring size, etc. may also be collected along with the ear data to better understand if there are patterns which may emerge. For example, analysis of the data may indicate that earpiece devices should be physically optimized for specific geographical regions of the world and could yet be further marketed based on age, weight, gender and even ring finger size.

The acquired data may also be useful for other areas such as: reconstructive and cosmetic surgery, acoustical modeling, head related transfer functions, eyewear design, goggle design (e.g. for skiing, hunting and/or swimming), face mask design (e.g., for skiing, medical and/or other face mask design), helmet design (e.g., for sports, motorcycles, and/or for combat), hearing protection, headwear for the apparel industry, hearing aids, communication equipment, and professional and consumer electronics devices which may include systems for transmission of sound as well as for picking up sounds and voices.

Exemplary CT images may be collected from among a portion of the many millions of head CT studies available in an electronically archived manner in diagnostic centers and hospitals throughout the world.

Earpiece devices of the present invention may be configured to fit in the EAC, the concha, behind the ear, at the orifice (i.e. an aperture of the ear anatomy), or in some combination thereof.

According to an exemplary embodiment, tragus measurements of the ear anatomy may be considered for determining an overall fit of the earpiece device. In some cases, an earpiece device design goal may be for the earpiece to be fitted behind (underneath) the tragus.

In many cases earpiece devices may partially protrude outside the orifice. Accordingly, it may be desirable to reduce a physical profile of the earpiece device. This may be the case for a passive earpiece (e.g., no electroacoustic components) which may be used for sleep. Often rubber, foam, other materials which offer elastic properties is inserted in to the orifice while the wearer attempts to push the earpiece device into the EAC. Based on the canal volume, shape, tortious paths locations of the first and second bends, the earpiece device may only travel a portion of a desired length. Thus the earpiece device may protrude from the orifice, into the concha and possible past the tragus. As such, when the wearer turns their head during sleep, the earpiece device may come in contact with a surface and may become dislodged. If the earpiece device were fitted distally within the concha bowl, when the user lies down, the earpiece device would not come in contact with the surface (because it would be shielded by the pinna and would stay in the canal).

Referring to FIG. 1, a functional block diagram of an exemplary anthropometric measurement system, designated generally as system 100, is shown. System 100 may determine statistical measurements 130 which may be useful for earpiece device design. System 100 may include surface extractor 102, automatic deformable surface registration unit 104 (also referred to herein as surface registration unit 104), statistical anthropometric measurement unit 106 (also referred to herein as statistical measurement unit 106), memory 108, controller 110 and image database 120. Surface extractor 102, surface registration unit 104, statistical measurement unit 106, memory 108, controller 110 and image database 120 may be coupled together via a data and control bus (not shown).

System 100 may be coupled to user interface 112 and display 114. Although user interface 112 and display 114 are illustrated as being external to system 100, one or more of user interface 112 and display 114 may be included as part of system 100. Although image database 120 is illustrated as being internal to system 100, image database 120 may be external to system 100. Although not shown, system 100 may be coupled to a remote location, for example via a global network (i.e., the Internet).

Surface extractor 102 may be configured to receive a plurality of images 122 from image database 120. The plurality of images 122 may represent a population of different individuals. Each image 122 desirably includes at least one ear anatomy (e.g., the left and/or right ear of an individual). As described further below with respect to FIG. 3, surface extractor 102 may extract a three-dimensional (3D) surface from each image 122, thus providing a plurality of extracted surfaces 124 from the respective plurality of images 122. Each extracted surface 124 may include a representation of at least one ear anatomy of respective image 122. The ear anatomy may include at least one of an EAC, a concha or a pinna.

Figure 5B:
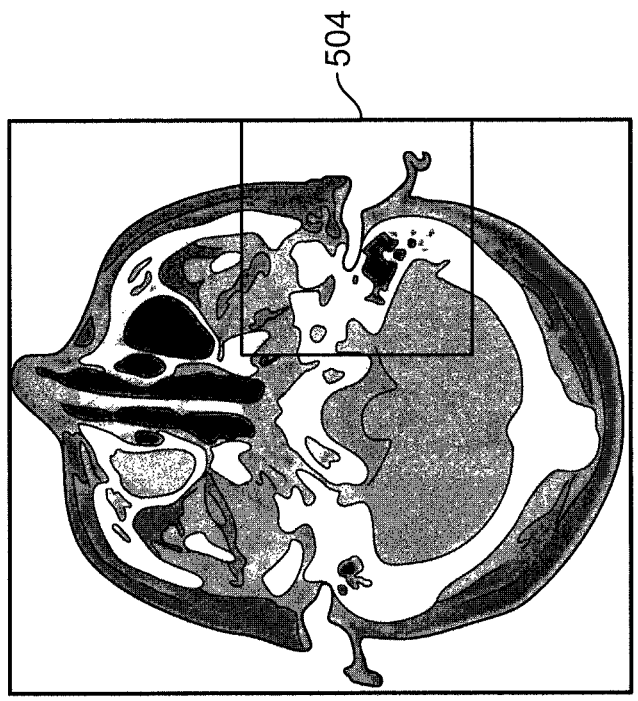
FIGS. 5A and 5B are example computer tomography (CT) images of a head illustrating an ear anatomy, according to an aspect of the present invention.
Figure 5A:
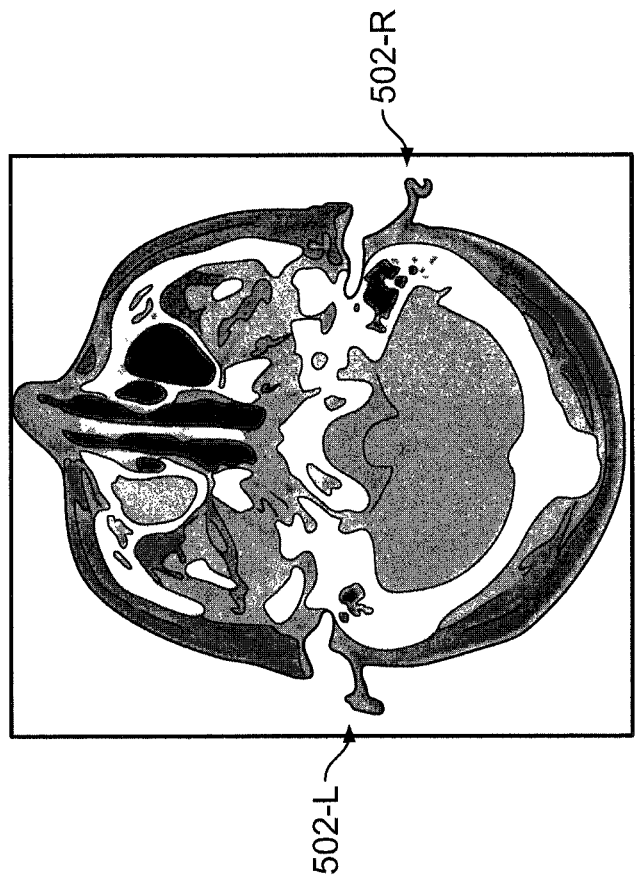

In an exemplary embodiment, image database 120 may store medical images. For example, system 100 may be developed from a large pool (e.g., thousands) of medical images (stored in image database 120), acquired with ethical consent from contributing institutions. For imaging the EAC and pinna, CT imaging may be used, as CT series imaging typically produces a strong contrast between ear tissue and the surrounding air, as shown in FIG. 5A. It is understood that CT imaging represents an exemplary embodiment, and that any suitable modality capable of capturing an image which includes an ear anatomy may be used. Images 122 may include, without being limited to, CT images, X-ray images, magnetic resonance (MR) images or ultrasound images. Although image database 120 is described as storing medical images, in general, image database 120 may store medical images or photographic images, either of which may be used by surface extractor 102. Accordingly, images 122 may include at least one of two-dimensional (2D) images or 3D images.

In an exemplary embodiment, image database 120 stores CT images. A CT series image typically consists of a large number of two-dimensional (2D) image slices. Each image slice may include, for example, 512×512 pixels. Each pixel may represent the density of the material being imaged. Stacking the slices together may form a 3D volume of data. Typically, the voxels in this volume have an anisotropic size, with out-of-plane resolution lower than in-plane resolution. In an exemplary embodiment, the slice thickness is less than about 2.5 mm, in order to capture fine surface details (which may be useful for subsequent measurements). The values in a CT image are typically normalized in Hounsfield Units (a quantitative scale measuring radiodensity). For example, in Hounsfield units, air has a value of about −1000, water has value of about 0, and bone has a value greater than about 700. Human tissues including soft tissue, fat, and muscle have Hounsfield units that typically vary between about −300 and about 100.

Dicom (Digital Imaging and Communications in Medicine) is a standard for handling, storing, printing, and transmitting information in medical imaging, and is a widely available format produced by modern medical imaging equipment. The Dicom format includes a header, which contains numerous fields (also known as "tags") that store additional information about the image, such as the scanning hardware, date, patient position, image size, etc. After the header, the actual pixels of the image are stored. The header information in the Dicom format may be useful for stratifying population data into one or more subpopulations, described further below with respect to FIG. 4. In an exemplary embodiment, medical images may be provided in Dicom format. It is understood, however, that the present invention is not limited to a Dicom format.

Surface registration unit 104 may receive extracted surfaces 124 from surface extractor 102, and may determine spatially registered surfaces 128. Surface registration unit 104 may include landmark identifier 116 and group-wise registration unit 118.

Landmark identifier 116 may receive extracted surfaces 124 and may identify one or more landmarks 126 from each extracted surface 124. Group-wise registration unit 118 may receive identified landmark(s) 126, and may generate spatially registered surfaces 128 based on identified landmark(s) 126. Landmark identifier 116 and group-wise registration unit 118 is described further below with respect to FIG. 2A and FIG. 4.

Statistical measurement unit 106 may receive spatially registered surfaces 128 from surface registration unit 104, and may determine at least one statistical measurement 130. Statistical measurement(s) 130 may include statistical measurements, for example, for ear canal, concha, tragus and/or pinna measurements representative of a population and/or at least one subpopulation within the population. Statistical measurement(s) 130 may include, without being limited to, at least one of a mean, a median, a standard deviation or a confidence interval (e.g., a 95% confidence interval). Statistical measurement(s) 130 may be compared between subpopulations or between a subpopulation and a population. Statistical measurement(s) 130 may be used to optimize at least one design parameter (for at least one subpopulation and/or a population) for designing an earpiece device. Accordingly, an earpiece device may be formed based on the optimized design parameter.

Figure 7B:
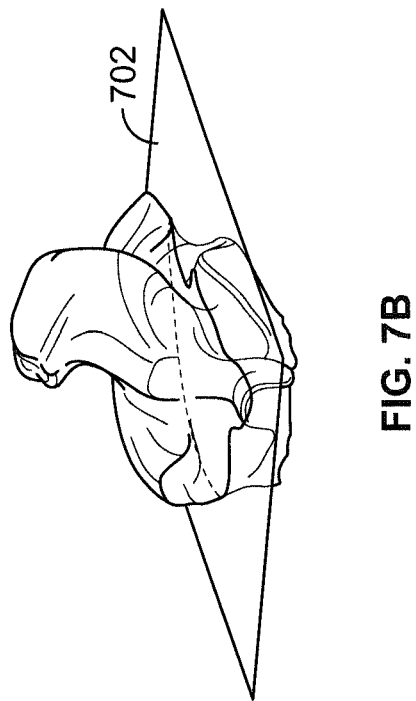
FIG. 7B is a 3D image of an example extracted surface illustrating a baseplane for identifying landmarks in the extracted surface, according to an aspect of the present invention.

Example canal measurements may include canal cross-sectional dimensions (such as a minimum length, a maximum length, an area) as a function of distance along the canal from the aperture (described further below in FIG. 8A) and canal orientation at the aperture relative to a reference plane (described further below in FIG. 7B). Example concha measurements include concha cross-sectional dimensions (such as a minimum length, a maximum length, an area) as a function of distance from the aperture, concha volume (e.g., in cubic centimeters) as a function of distance from the aperture and a concha depth (e.g., measured from the reference plane to the concha pit). Example tragus measurements include a tragus thickness, a tragus height, a tragus width, a distance from a tragus bottom to an aperture centroid (described further below) and a distance from an intertragal notch to the aperture centroid. An example pinna measurement may include a distance between the pinna an the skull (which may be useful for behind-the-ear devices).

Memory 108 may be configured to store at least one of extracted surfaces 124, identified landmarks 126, spatially registered surfaces 128 or statistical measurements 130 (for at least one subpopulation and/or a population). Although image database 120 and memory 108 are illustrated as being separate components, memory 108 may also include image database 120. Memory 108 may include, for example, a magnetic disk, an optical disk or a hard drive.

Controller 110 may be coupled to one or more of surface extractor 102, surface registration unit 104, statistical measurement unit 106, memory 108 and image database 120, to control surface extraction, surface registration and statistical measurement determination. Controller 110 may stratify the population data into one or more subpopulations. Controller 110 may also optimize at least one design parameter based on statistical measurement(s) 130. Controller 110 may include, for example, a logic circuit, a digital signal processor or a microprocessor. It is understood that one or more functions of surface extractor 102, surface registration unit 104 and/or statistical measurement unit 106 may be performed by controller 110.

User interface 112 may include any suitable user interface capable of providing parameters associated with one or more of surface extractor 102, surface registration unit 104 and statistical measurement unit 106 and image database 120. User interface 112 may include, for example, a pointing device, a keyboard and/or a display device.

Display 114 may include any suitable display device capable of presenting at least one of images 122, extracted surfaces 124, identified landmarks 126, spatially registered surfaces 128 or statistical measurement(s) 130. Although user interface 112 and display 114 are illustrated as separate devices, it is understood that the functions of user interface 112 and display 114 may be combined into one device.

Suitable surface extractor 102, surface registration unit 104, statistical measurement unit 106, memory 108, controller 110, user interface 112, display 114 and image database 120 may be understood by the skilled person from the description herein.

Figures 2A, 2B:
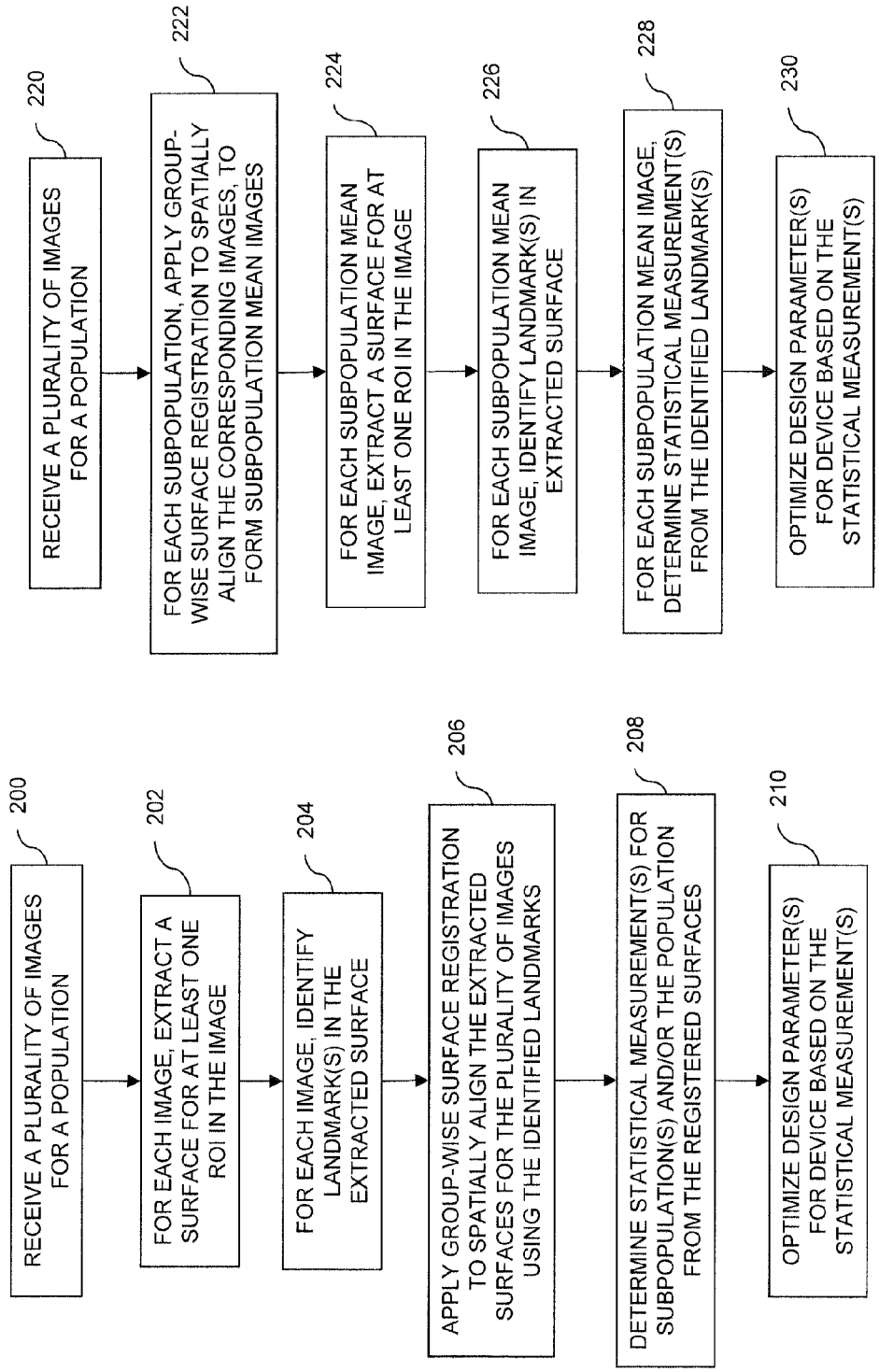
FIGS. 2A and 2B are flow chart diagrams illustrating exemplary methods for designing an earpiece device, according to aspects of the present invention.

Referring next to FIG. 2A, an exemplary method for designing an earpiece device is shown. The steps illustrated in FIG. 2A represent an example embodiment of the present invention. It is understood that certain steps may be performed in an order different from what is shown.

At step 200, a plurality of images for a population of individuals is received, for example, from image database 120 (FIG. 1). At step 202, for each image, a 3D surface is extracted for at least one region of interest (ROI) in the image, for example, by surface extractor 102 (FIG. 1). Each 3D surface represents a ROI (for example, an ear anatomy) that is included in the corresponding image. Accordingly, at step 202, a plurality of extracted surfaces are determined corresponding to the plurality of images.

At step 204, for each image, at least one landmark is identified in the corresponding extracted surface, for example, by landmark identifier 116 (FIG. 1). At step 206, group-wise surface registration is applied to the plurality of extracted surfaces (step 202) based on the identified landmark(s) (step 204). The group-wise surface registration may be applied to bring the extracted surfaces into spatial alignment. The group-wise surface registration may be performed, for example, by group-wise registration unit 118 (FIG. 1).

At step 208, at least one statistical measurement is determined for at least one subpopulation and/or the population from the registered surfaces (step 206), for example, by statistical measurement unit 106 (FIG. 1). At step 210, at least one design parameter is optimized for an earpiece device based on the statistical measurement(s) (step 208), for example, by controller 110. The earpiece device may be formed using the optimized design parameter. The design parameter may include a shape of the earpiece device relative to a shape of at least a portion of the earpiece surface. For example, a shape of the earpiece device may be optimized with respect to its fit in the concha. Other examples include optimizing a wire positioning on the earpiece device and/or optimizing an earpiece size.

By optimizing the design parameter, the earpiece device may provide an improved fit across a population (and/or a subpopulation). The improved fit may also provide one or more of: an improved bass response (by a transducer of the earpiece device); an improved sound pressure level (SPL) transfer to the eardrum (by a transducer of the earpiece device); a reduced intermodulation distortion (by operating a speaker in the earpiece device at lower drive levels); an improved ambient sound attenuation; an enhanced comfort; a reduced physical irritation of the earpiece device; a reduction of earpiece device from being dislodged from the concha; an improved stability of the earpiece device; a long term wearability of the earpiece device; and a lower physical profile of earpiece device in the concha. The bass response, SPL transfer, intermodulation distortion and ambient sound attenuation represent acoustical qualities of the earpiece device. For example, an improved earpiece device coupling in the ear anatomy (by improving the fit of the earpiece device) may improve the acoustical qualities of the earpiece device.

Referring next to FIG. 2B, an exemplary method for designing an earpiece device is shown, according to another embodiment of the present invention. The steps illustrated in FIG. 2B represent an example embodiment of the present invention. It is understood that certain steps may be performed in an order different from what is shown.

At step 220, a plurality of images for a population of individuals is received, for example, from image database 120 (FIG. 1). At step 222, for each subpopulation, a group-wise surface registration is applied to images from the plurality of images (step 220) corresponding to the subpopulation, to form a mean image for each subpopulation. Step 220 may be performed, for example by group-wise registration unit 118 (FIG. 1).

At step 224, for each subpopulation mean image, a 3D surface is extracted for at least one ROI (e.g., an ear anatomy), for example, by surface extractor 102 (FIG. 1). Accordingly, at step 224, an extracted surface is obtained for each subpopulation mean image (step 222).

At step 226, for each subpopulation mean image, at least one landmark is determined in the corresponding extracted surface, for example, by landmark identifier 116 (FIG. 1). At step 228, at least one statistical measurement is determined for each subpopulation from the extracted surfaces (step 224) using the identified landmark(s) (step 226), for example, by statistical measurement unit 106 (FIG. 1). At step 230, at least one design parameter may be optimized for an earpiece device based on the statistical measurement(s) (step 228), for example, by controller 110. The earpiece device may be formed using the optimized design parameter.

In FIG. 2B, the group-wise registration (step 222) is first applied to the set of CT images. Subpopulation mean images are then processed. In FIG. 2B, the registration of the images may involve registering parts of the image that may not be of interest (such as the brain or skull), which may distort the geometry for the anatomy of interest (e.g. the EAC, concha and/or pinna).

Referring next to FIG. 3, an exemplary method for extracting a surface from an image (step 202 in FIG. 2A) is shown. The steps illustrated in FIG. 3 represent an example embodiment of the present invention. It is understood that certain steps may be performed in an order different from what is shown.

At step 300, at least one ROI (for example, an ear anatomy) is determined. In an exemplary embodiment, this step may identify the left and right ears and their respective EACs in a CT image of the head. An example CT image of the head is provided in FIGS. 5A and 5B. The CT image includes 3D (volume) data. FIGS. 5A and 5B show a single slice through the volume data. The EAC and external ear are visible in FIG. 5A. In FIG. 5A, left pinna 502-L and right pinna 502-R may be observed as protrusions. In FIG. 5B, box 504 is a ROI which encloses an ear and its EAC. As the data is three-dimensional, the bounding box 504 is a 3D object. Identification of 3D bounding box 504 may be done manually. However, given the large number of medical images, it may, more preferably, be performed automatically using a pattern recognition algorithm.

In one example approach, the pinna of each ear may first be identified based on its left/right location on axial slices. The pinna consists of human tissue, and therefore has a tissue-like Hounsfield unit. The pinna (e.g., pinna 502 in FIG. 5A) also is a protrusion on the left side or right side of the image, assuming standard head CT scanning protocols. From the detected protrusion, air in the concha and EAC may then be extracted, going towards the tympanic membrane. A bounding box 504 (FIG. 5B) may be fit to the spatial positions of the pinna, EAC, concha, and tympanic membrane. Alternative embodiments may involve a template matching approach or extraction of a set of discriminative features, followed by classification. Additional checks may be run on the bounding box to handle outliers or erroneous data, for example, when the ear is not completely in the field of view of the scanner.

Additionally, step 300 may identify which ear is the left and which is the right. While the Dicom header, for example, may provide useful information for this purpose, it is possible for the CT machine operator to incorrectly indicate the patient position in the scanner, and therefore the Dicom header might not be faithful to the true patient position. An additional check may be performed to verify the patient positioning and thereby determine if the ear identified on the right side of the volume is the right ear or left ear, and similarly for the ear identified on the left side of the volume.

According to an exemplary embodiment, the set of axial CT slices may be sorted based on the "Slice Location" Dicom tag, 0020-1041 in each Dicom header file. Then, the set of slices may be stacked to create a 3D volumetric dataset, so that the slice with the minimal slice location is at the bottom of the stack, and the slice with the highest slice location is at the top of the stack. From this 3D stack of 2D axial slices, the nose and eyes may be detected using template matching. With the eyes and nose located, the way the patient is facing may be identified to determine if the patient is in the prone or supine position. Furthermore, because the eyes are above (proximal to the patient's head) the ears, it can be determined if the patient is in a head-first or foot-first position in the scanner. For computational efficiency, the above nose and eye detection methods may be implemented on downsampled versions of the images.

Figure 6B:
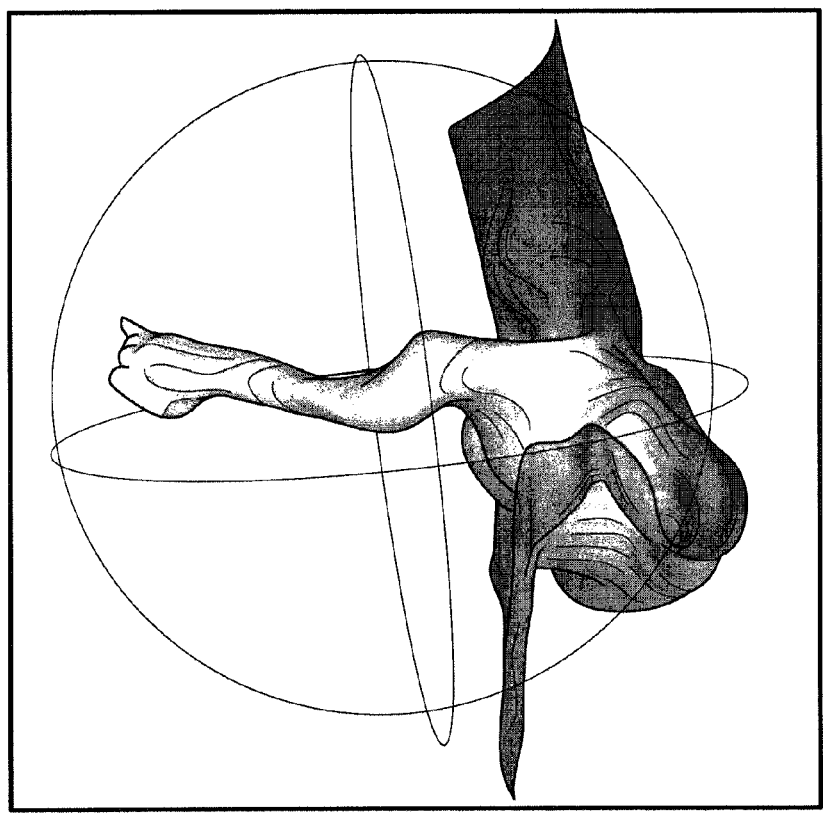
FIGS. 6A and 6B are 3D images of example extracted surfaces, according to an aspect of the present invention.
Figure 6A:
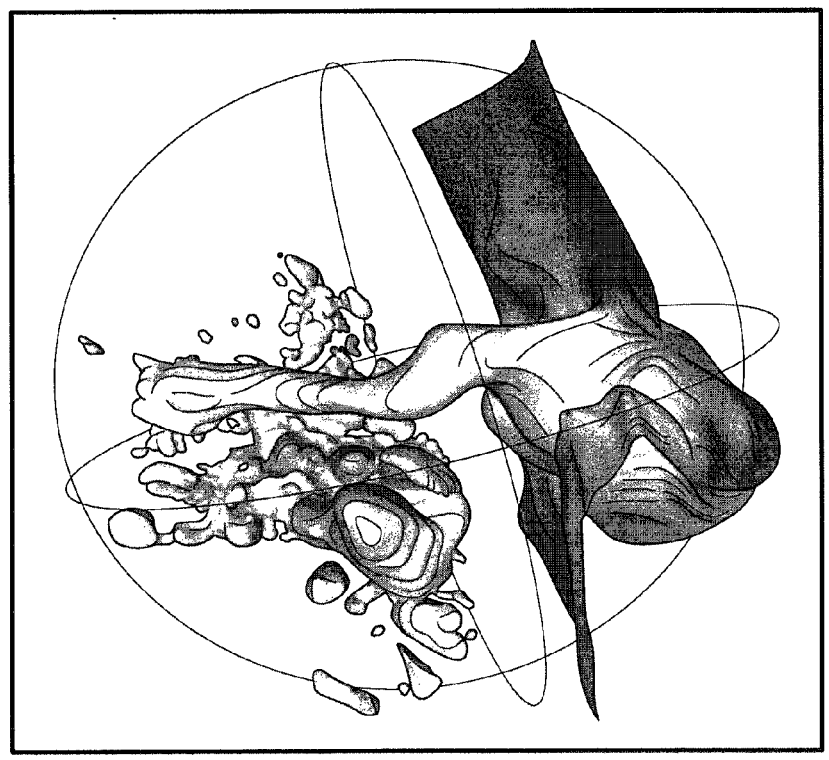

At step 302, a 3D surface may be extracted from the at least one ROI (for example, from bounding box 504 shown in FIG. 5B). From each bounding box (one surrounding the left ear and another surrounding the right ear), a subvolume of voxel data may be extracted. From this subvolume, a 3D surface can be extracted using an isosurface extraction algorithm such as marching cubes. Marching cubes are described in a publication by Lorensen et al. entitled "Marching Cubes: A high resolution 3D surface construction algorithm," *Computer Graphics*, Vol, 21, Nr. 4, July 1987. The extraction algorithm may provide a surface, represented as a triangular mesh, which models the interface between air and tissue. An example extracted surface is shown in FIG. 6A, (In an exemplary embodiment, the surface extraction step may use voxel size information available in the CT Dicom header, so that the resulting extracted surface has coordinates which may be measured in millimeters.)

At step 304, disconnected regions may be removed from the extracted surface. Due to the other air-filled regions near the EAC such as the inner ear, there may be considerable excess geometry included in the model. Step 304 may perform a "clean-up" step to remove disconnected air-filled regions as well as those attached (due to a partial volume effect) to the model. To remove disconnected regions, a connected component analysis may be performed on the triangular mesh to identify groups of triangles that are connected in 3D, Connected component analysis is described in a publication by Dillencourt et al. entitled "A General. Approach to Connected-Component Labeling for Arbitrary Image Representations," *Journal of the ACM*, 39(2), 1992. This step typically reveals numerous components. The cardinality of each component may be determined as the number of connected triangles (or alternatively, vertices) in the component. The component with the largest cardinality may be retained, with remaining components being deleted.

At step 306, spurious excess geometry may be removed. Nearer to the tympanic membrane, there may be numerous air-filled regions of the inner ear. Even after the connected component analysis described above (step 304), there may still exist spurious excess air-filled geometry connected to the largest component, due to a partial volume effect in CT imaging. An additional geometric filtering may be performed to eliminate such geometry. The filter may be implemented using mathematical morphology. Mathematical morphology is described in a publication by Lomenie et al. entitled "Morphological Mesh Filtering and alpha-Objects," *Pattern Recognition Letters*, 29(10) 2008, Specifically, an erosion operation may disconnect the canal from the excess geometry. After the erosion, another connected component analysis may be performed to detect if a disconnection occurred. If so, only the largest component may be retained. The largest component may then be dilated to restore a shape similar to the original surface. The original surface may be retained except near the location of the disconnection, where the dilated surface is used instead. An example result of the surface clean-up steps (steps 304 and 306) (performed on the extracted surface of FIG. 6A) is shown in FIG. 6B. Note that, in FIG. 6B, the ear surface is now a single surface and is represented by a single, connected 3D component.

At step 308, it is determined whether the surface is valid. The extracted surface desirably contains the anatomical structures of the ear that are to be measured. However, this may not always be the case, due to a variety of complicating factors. First, as mentioned above, the entire ear (including the pinna and EAC) might not be in the CT series as it may not be in the field of view when scanned. If the patient's head is placed in a frame during scanning, objectionable deformation of the pinna and canal may result. Due to wax build-up or deviated canals, some patients might not have an extractable EAC surface. Step 308 may determine if the surface is valid, so that such problematic surfaces are identified and eliminated from further analysis as they may skew statistical measurements in system 100 (FIG. 1).

One example approach to determining if a surface is valid may be based on landmark identification (step 204 in FIG. 2A and described further below). Landmarks for the anatomic regions used for surface analysis may be identified. Landmarks may include the concha, tragus, anti-tragus, and anti-helix, along with the aperture and canal tip. If the landmarks are not present in the data, the data set may be rejected. If the landmarks are present, simple measurements may be made to ensure that the surface geometry falls within normal ranges. Example measurements may include a distance from the canal tip to the aperture, a distance between the tragus and anti-tragus, a distance between the anti-helix and the tragus, and/or a distance between the tragus and the aperture. Surfaces that do not have measurements in a predetermined range may be filtered out (i.e., excluded) from further processing.

If it is determined, at step 308, that the surface is valid, step 308 proceeds to step 204 (FIG. 2A). If it is determined, at step 308, that the surface is not valid, step 308 may proceed to step 310. At step 310, the surface is excluded from further processing.

Referring next to FIG. 4, an exemplary method for applying group-wise registration (step 206 in FIG. 2A) is shown. The steps illustrated in FIG. 4 represent an example embodiment of the present invention. It is understood that certain steps may be performed in an order different from what is shown.

At step 400, at least one identified landmark (step 204 in FIG. 2A) is received, for example, from landmark identifier 116 (FIG. 1). Referring back to step 204 in FIG. 2A, landmark identification is described further below. In an exemplary embodiment, prior to step 204, there is a set of N right ear surfaces, and additionally, a set of M left ear surfaces (where M and N are each integers greater than or equal to 1). Note that N is not necessary equal to M, as some surfaces may be filtered out due to the complications mentioned above. The description below relates to the identification of landmarks in one of the sets (either M or N). It is understood that the landmark identification may be similarly performed on the remaining set of ear surfaces. For each surface in a set of ear surfaces, key anatomic landmarks on the surface may be automatically identified. These landmarks may be used in registration (spatial alignment) of ear surfaces (described in FIG. 4).

Figure 7A:
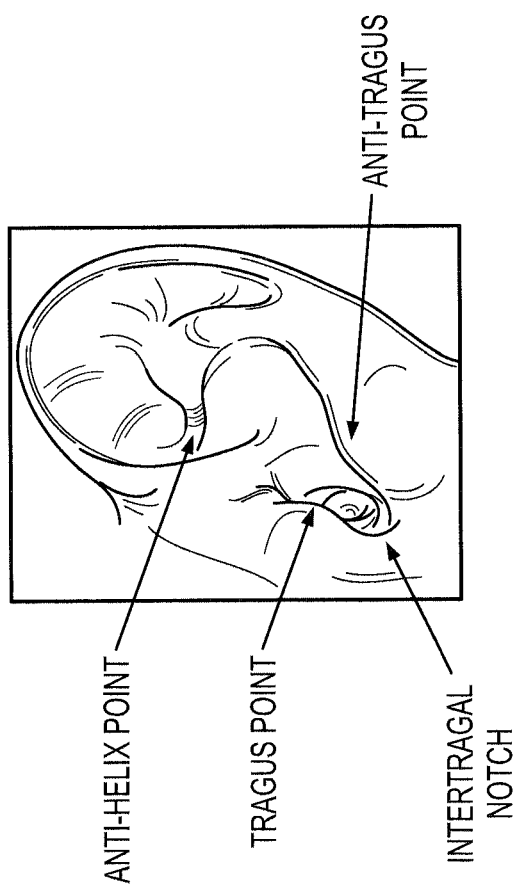
FIG. 7A is an image of an example ear anatomy illustrating various landmarks, according to an aspect of the present invention.

Surface-based landmark detection may be used for automated shape analysis and transformation. It is desired to robustly identify landmarks given an anatomical surface. According to an exemplary embodiment, four feature points may be automatically identified. The four feature points may include the tragus, antitragus, antihelix, and intertragal notch. FIG. 7A is an image of an example ear anatomy illustrating these four feature points. These points may be automatically identified based on their local 3D surface curvature. Techniques to automatically identify the feature points are described in a publication by Baloch et al. entitled "Automatic Detection of Anatomical Features on 3D Ear Impressions for Canonical Representation," *International Conference on Medical Image Computing and Computer Assisted Intervention* (MICCAI), 2010.

Given the four identified feature points, a baseplane may then be defined as a plane passing through these points. FIG. 7B is an image of an example extracted surface illustrating baseplane 702 which passes through the tragus, antitragus, and antihelix points. Baseplane 702 serves as a reference plane for subsequent computations.

Figure 8B:
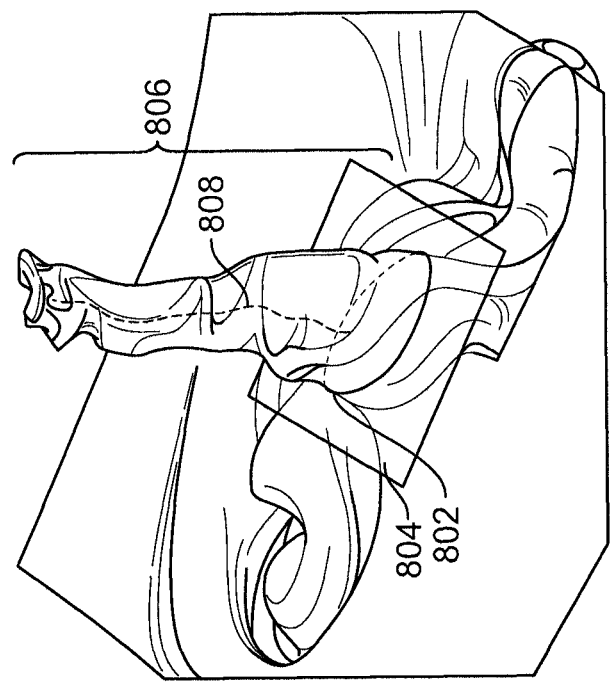
FIG. 8B is a 3D image of an example extracted surface illustrating an identified canal and canal centerline, according to an aspect of the present invention.
Figure 8A:
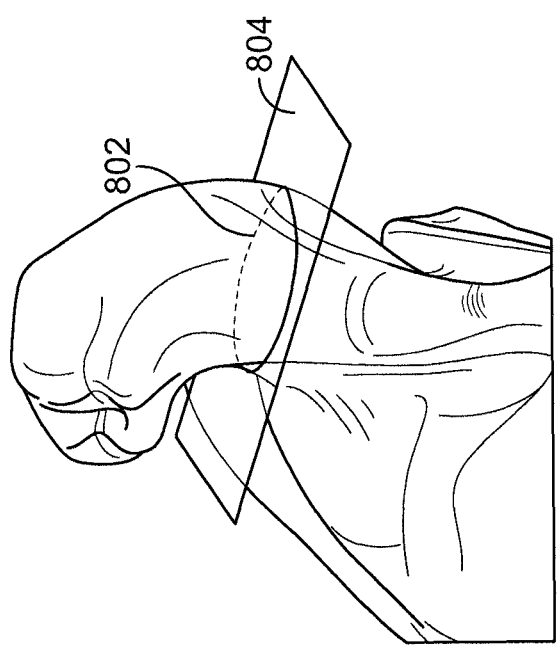
FIG. 8A is a 3D image of an example extracted surface illustrating an identified aperture, according to an aspect of the present invention.

For the design of in-ear devices, one of the most important landmarks of an ear surface is the aperture. The aperture separates the ear canal from the outer ear. According to an exemplary embodiment, the aperture may be modeled as a surface contour resulting from the intersection of a plane (the aperture plane) with the ear surface. For example, FIG. 8A is a 3D image of an example extracted surface that includes aperture 802 and aperture plane 804. Aperture plane 804 may be detected automatically. Techniques for automatically detecting aperture plane 804 are described in a publication by Zouhar et al. entitled "Anatomically-Aware, Automatic, and Fast Registration of 3D Ear Impression Models," the *Third International Symposium on 3D Data Processing, Visualization and Transmission* (3DPVT) 2006. Once aperture 802 is identified, the canal surface may include all geometry in a positive half-space of the aperture plane and in a single connected component that touches the aperture contour. For example, FIG. 8B is a 3D image of an example extracted surface Including canal 806. Canal 806 extends from aperture 802 away from the baseplane. The canal tip may be identified as the point on the canal that is farthest from the baseplane.

Next, a centerline running through the canal may be determined. In an exemplary embodiment, an initial centerline path may be defined as a line extending from the aperture centroid to the canal tip. Note that the centroid of a geometric object is simply the average of all the vertex positions in the object. In this case, the aperture centroid may be the 3D position that represents the average position of all points on the aperture contour.

The initial centerline path may then be iteratively refined. For each iteration, the path may be sampled to produce a set of points. At each point, a plane orthogonal to the path tangent may be defined, and intersected with the mesh. This may result in several intersection contours. The intersection contour closest to the path may be maintained, and its centroid may be computed. The set of centroid positions may be fit to a spline to produce a refined path. The path may be further refined in this fashion until convergence is reached or a fixed number of iterations has been achieved. An example centerline 808 determined in this manner is shown in FIG. 8B.

Figure 9C:
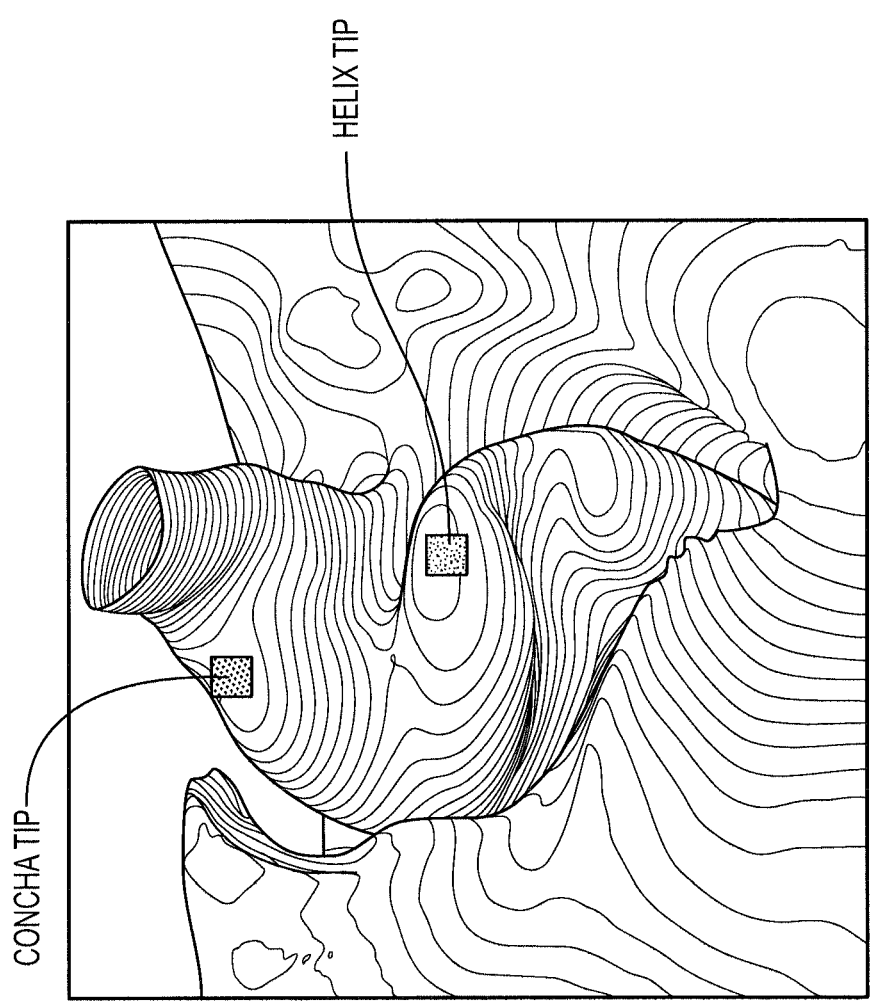
FIG. 9C is a 3D image of an example extracted surface and level set curves, according to an aspect of the present invention.

It is understood that the set of landmarks is not limited to those landmarks described above. At least one additional landmark may include, without being limited to, the pinna, the helix root, the canal first bend, the canal second bend, or one or more application-defined features. In general, landmarks may be selected to identify specific geometries, volumes, ratios, radius, and paths and distances of the human ear and its relationship to the head and/or skull. FIGS. 9A and 9B are 3D images of example left ear surfaces of two different individuals. FIGS. 9A and 9B also illustrate various identified landmarks. These landmarks include the tragus, the ant-tragus, the intertragal notch, the anti-helix, the mesh centroid, the aperture contour (a closed contour) and the canal centerline (an open contour). FIG. 9C is a 3D image including an example surface and a plurality of level set curves. The concha tip and helix tip, shown in FIG. 9C, may be detected by analyzing the level set curves. Analysis of the level set curves is described in the publication by Baloch et al.

Referring back to FIG. 4, at step 402 a transformation is applied to each surface based on the identified landmarks. Each surface may have a different position and orientation in 3D space, in addition to a different overall shape. Step 402 of the registration may be based on the identified aperture (step 204 in FIG. 2A). A rigid transformation (composed of a 3D rotation and 3D translation, providing six degrees of freedom) may be applied to each surface. For example, FIGS. 10A and 10B are 3D images of surfaces before (FIG. 10A) and after (FIG. 10B) the transformation. Initially, the 3D surface may have an arbitrary position and orientation, as shown in FIG. 10A. The transformation may be applied such that the aperture centroid of the surface is located at the origin and the aperture contour is in the xy plane, with a normal of the aperture plane pointing in the direction of the canal tip being along the positive z axis, as shown in FIG. 10B. The surface is rotated about the z axis so that the intertragal notch is in the xz plane with a positive x coordinate. Step 402 may be performed for all surfaces separately, in order to bring the surfaces into a common coordinate system for further processing.

At step 404, a group-wise surface registration is applied to spatially align all of the surfaces. In general, surface registration determines a spatial mapping between surfaces so that their corresponding features become aligned. FIGS. 11A and 11B are illustrations of an example surface registration process for two surfaces. In FIG. 11A, the surface registration is shown schematically in two dimensions, for simplicity. FIG. 11A demonstrates a transformation T that transforms points from surface $S_1$ to surface $S_2$. The mapping is bijective, meaning it is invertible so that points from $S_2$ may be mapped to $S_1$. As shown in FIG. 11B, the transformation T may be represented as a smooth, non-rigid deformation of space, here illustrated as a warping of a regular grid. Points from surface $S_1$, when transformed by T, will align to surface $S_2$. Given the large variability of anatomic shape, this mapping between ear surfaces is necessarily non-linear. Corresponding detected features may be used in a data term, while regularization may be employed so that the deformation is smooth in 3D space. The mapping itself may be represented using B-splines to define a smooth, non-rigid transformation T.

However, for the exemplary embodiment of the ear anatomy, there are more than two surfaces (generally there are N surfaces). The task of group-wise registration is a task of co-registration, that is, bringing all N surfaces into spatial alignment. One way to achieve this is to compute a registration $T_{ij}$ for all possible pairs of surfaces $S_i$ and $S_j$ (i not equal to j). However, such an approach is typically computationally intensive, because the number of unique pairs of surfaces grows combinatorially with N.

A more computationally efficient approach initially selects one surface as the target surface. Then all remaining surfaces in the set may be registered to the target. At this stage, a mean surface is computed using all registrations, and the process is repeated, however, this time using the computed mean surface as the template. The group-wise registration may continue in this manner until the set of registrations converge and the mean surface no longer changes on successive iterations.

Figure 12:
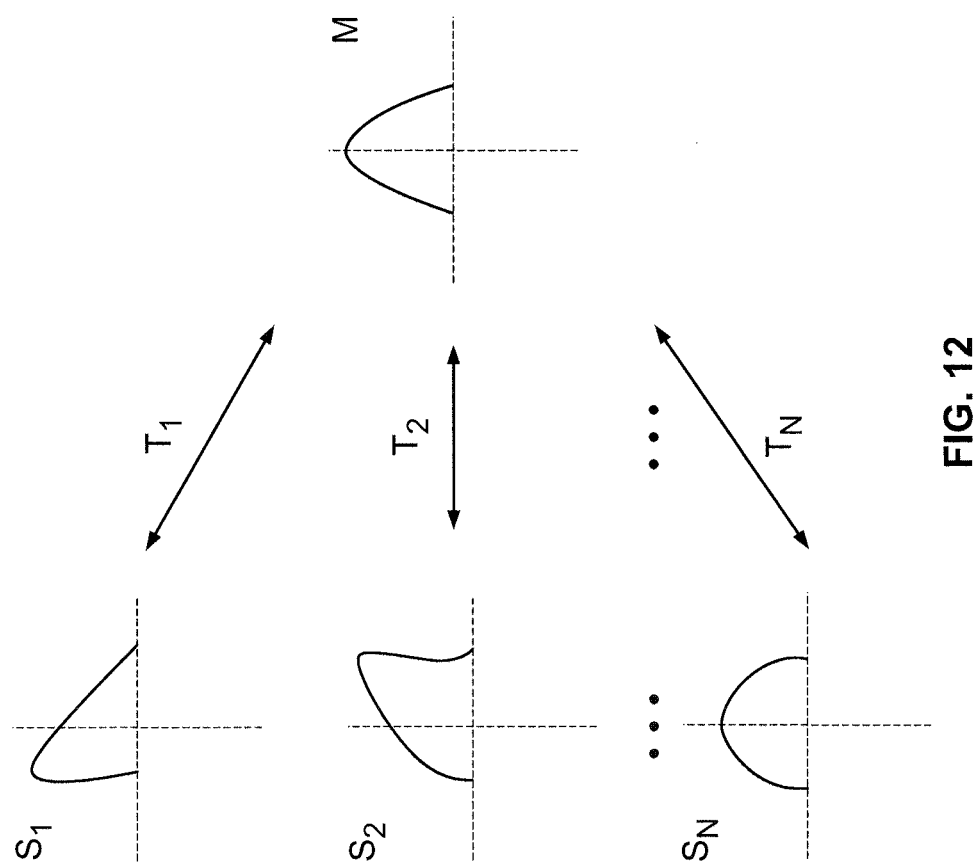
FIG. 12 is an illustration of an example group-wise registration process for a plurality of surfaces, according to an aspect of the present invention.

An example mean surface upon convergence is shown in FIG. 12. In FIG. 12, the group-wise registration is depicted schematically in 2D for simplicity. A set of N surfaces ($S_1$, $S_2$, . . . , $S_N$) are spatially aligned to the mean surface M. For each surface $S_i$, there is a corresponding bijective transformation $T_i$ that maps $S_i$ to the mean surface M.

At step 406, the surfaces may be stratified into at least one subpopulation. An aspect of the present invention is the stratification of the data. Stratification is defined as a decomposition of the data into different groups (subpopulations), based on gender, age, ethnicity, weight, or other factors. For example, one group may be men and another group may be women. For product design, it may be of interest to know if the measurements differ between these groups, and if so, by how much. For this purpose, it may be helpful to know the mean surface for each stratification, and how the surfaces within the subpopulation forming the stratification deviate from the subpopulation mean. The subpopulations may be identified from header information associated with each image. Thus, images may be selected as belonging to a subpopulation based on the header information.

In one exemplary embodiment, the group-wise registration may be performed on all datasets, without regards to any stratification. In this case, there may be one transformation $T_i$ between surface $S_i$ and the group mean M. A subpopulation mean may be computed based on the subset of surfaces in a given stratification. For example, the mean male surface may be computed from the set of male surfaces and their corresponding transformations to the population mean.

In another exemplary embodiment, separate group-wise registrations may be performed for each subpopulation. For example, the group-wise registration may be performed for all of the male surfaces, and a mean male surface may be generated. Separately, another group-wise registration may be performed for all the female surfaces, and a mean female surface may be generated. This approach may involve more computation, as for a given surface, there may be multiple deformation fields generated, one for each stratification. However, this approach may be more robust as surfaces within a subpopulation may exhibit less variation.

Referring back to FIG. 2A, after the group-wise registration (step 206), a set of 3D surfaces may be extracted and registered for various subpopulations of interest (at step 208). The subpopulation mean surface itself may be used for product design (at step 210), because it encapsulates an average shape for a given subpopulation (e.g., women, men, Asian, Caucasian, etc.).

For example, a measurement of interest may be the largest diameter of the aperture. For product design, one may be interested if this measurement differs between men and women, and if so, by how much. Given the male mean surface, the aperture contour may be identified and the largest diameter may be measured. The same analysis may be performed on the female mean surface. Then, the two measurements may be compared and may subsequently be used for optimizing a design parameter for an earpiece device.

Furthermore, a set of deformation fields may provide information regarding variation within the data. A standard deviation about the mean surface may encapsulate the degree of deformation for the data in the set. From this, statistical surfaces such as lower and upper confidence interval surfaces (e.g., a 95% confidence interval) may be determined, for example, assuming a parametric distribution (i.e., a Gaussian distribution). Alternatively, non-parametric techniques such as bootstrapping may be used to determine the statistical surfaces. The statistical surfaces may be useful in product design (step 210) as they provide a characterization not only of an average surface geometry for a subpopulation but also its variation within the subpopulation. This way, a design parameter may be optimized for a subpopulation such that it fits the majority of people (within a certain confidence interval) of the subpopulation.

Figure 13:
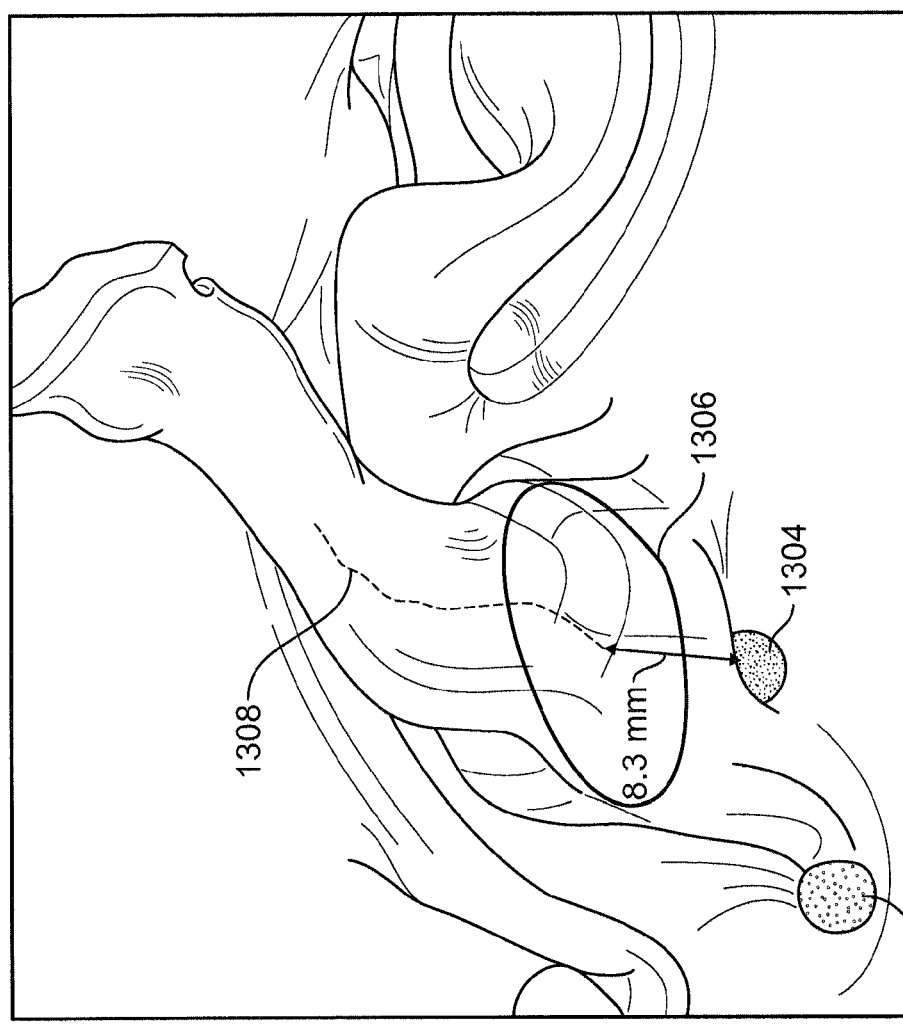
FIG. 13 is a 3D image of an example extracted surface illustrating a statistical measurement, according to an aspect of the present invention.

The statistical measurements (including the mean surface and the deformation fields) may be performed interactively or by programmable measurements. FIG. 13 is a 3D image of a mean surface which may be used for interactive measurements. In FIG. 13, intertragal notch 1302, tragus 1304, aperture 1306 and canal centerline 1308 are shown on the mean surface. An example of an interactive measurement may include a user indicating two points on the mean surface (for example, by mouse clicks on a display such as via user interface 112 (FIG. 1) and display 114). In the example, a user may indicate a distance between tragus 1304 and an aperture centroid (at the base of canal centerline 1308). Based on the indicated points, statistical measurement unit 106 (FIG. 1) may report the distance between the two points. For example, statistical measurement unit 106 may indicate the measurement by the double arrowed line and with the text "8.3 mm." Alternatively, statistical measurement unit 106 (FIG. 1) may perform programmable measurements on the surface by automatically determining the endpoints used to form the measurement.

A set of sample measurements is provided below in Table 1. The measurements are formed from a set of 63 CT images. The images were obtained from routine clinical scanning using bone and soft tissue scans of the head using GE CT scanning hardware and a varying slice thickness between 0.63 mm and 2.5 mm. The CT images were obtained with ethics approval from the contributing hospital. For each image, the left ear is extracted from each dataset and processed to produce the measurements in Table 1. The data is stratified into two subpopulations; one consisting of males (35 patients), and the other consisting of females (28 patients).

The measurements describe dimensions of the concha, including its length, width, depth in mm, and volume in $mm^3$. In addition to the mean measurement, other statistical measurements are provided, including the median, standard deviation (Std), and 95% confidence interval (CI). The stratification in Table 1 shows that women have smaller conchas than men for the given dataset. This result, and the measurements shown in Table 1, may be useful for the design of in-ear products such as earpiece devices.

TABLE 1

Example Concha Measurements

|  | Length | Width | Depth | Volume |
|---|---|---|---|---|
| Male (n = 35) | | | | |
| Mean | 15 | 20.26 | 10.52 | 2440.07 |
| Median | 15.22 | 19.83 | 10.66 | 2471.85 |
| Std | 2.14 | 3.25 | 1.28 | 620.6 |
| 95% CI lower | 10.81 | 13.88 | 8 | 1223.7 |
| 95% CI higher | 19.19 | 26.64 | 13.03 | 3656.43 |
| Female (n = 28) | | | | |
| Mean | 12.51 | 18.3 | 9.04 | 1905.86 |
| Median | 12.69 | 18.41 | 8.78 | 1784.12 |
| Std | 1.82 | 2.78 | 1.24 | 486.43 |
| 95% CI lower | 8.94 | 12.86 | 6.61 | 952.45 |
| 95% CI higher | 16.08 | 23.74 | 11.48 | 2859.26 |

Figure 14B:
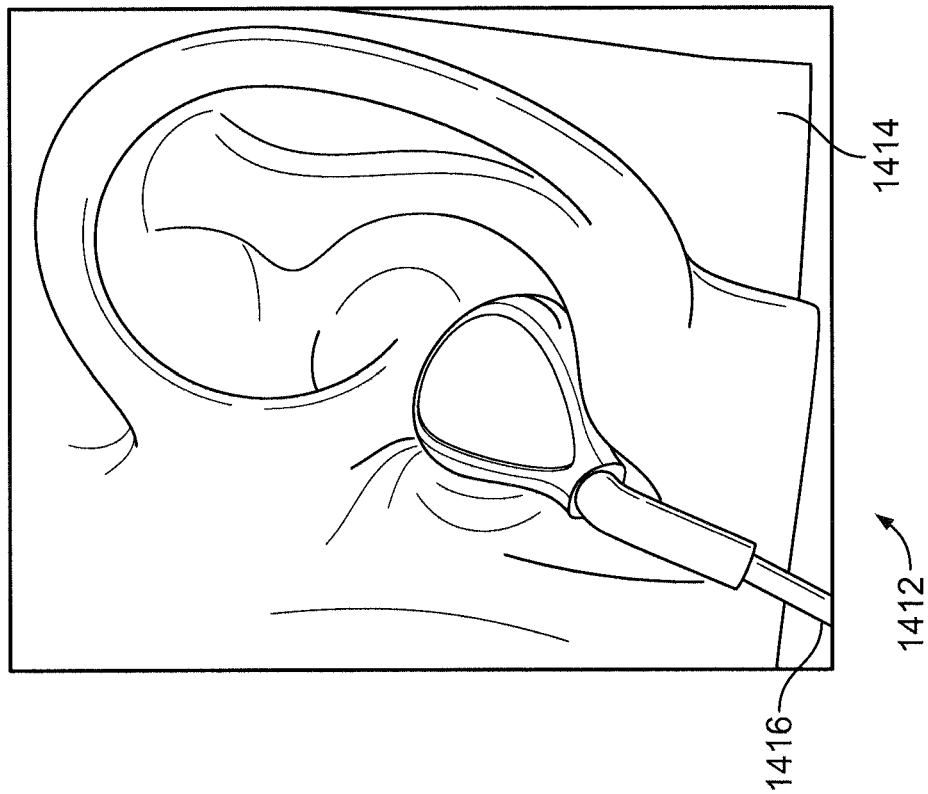
FIGS. 14A and 14B are 3D images of example mean surfaces with a shape of an earpiece device design optimized for the mean surfaces, according to an aspect of the present invention.
Figure 14A:
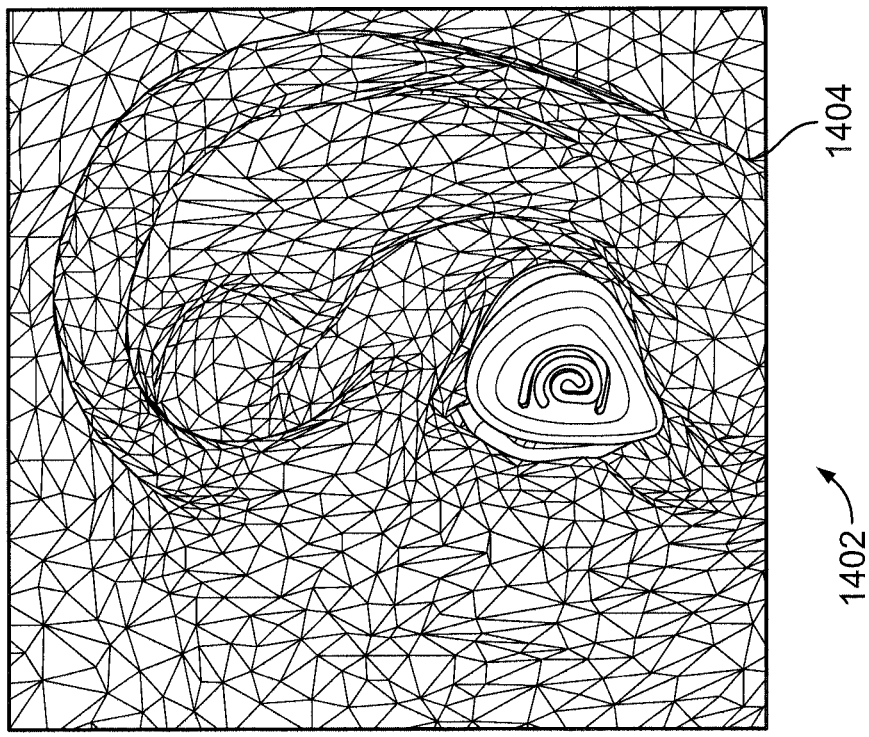
Figure 15A:
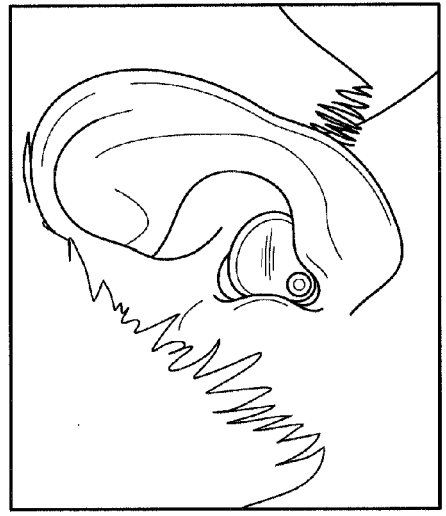
FIGS. 15A, 15B, 15C and 15D are example images of ears of different individuals with shape optimized earpiece devices fitted in each ear, according to an aspect of the present invention.
Figure 15B:
Figure 15C:
Figure 15D:

Referring to FIG. 14A, example earpiece device 1402 is shown fitted in mean surface 1404. Mean surface 1404 is determined for a population as described above with respect to FIG. 2A. The population is clustered according to critical dimensions of the ear. Earpiece device 1402 is designed for shape optimization in the concha (specifically targeting the clusters). FIG. 14B is similar to FIG. 14A, except that earpiece device 1412 includes wire 1416. In FIG. 14B, earpiece device 1412, including wire 1416, is shape optimized for mean surface 1414.

Referring to FIGS. 15A-15D, example images of ear anatomies of different individuals are shown. An earpiece device (shown in each of the ear anatomies) may be shape optimized, for example, as described above in FIG. 2A, to fit in each of the different ear anatomies.

Figure 16A:
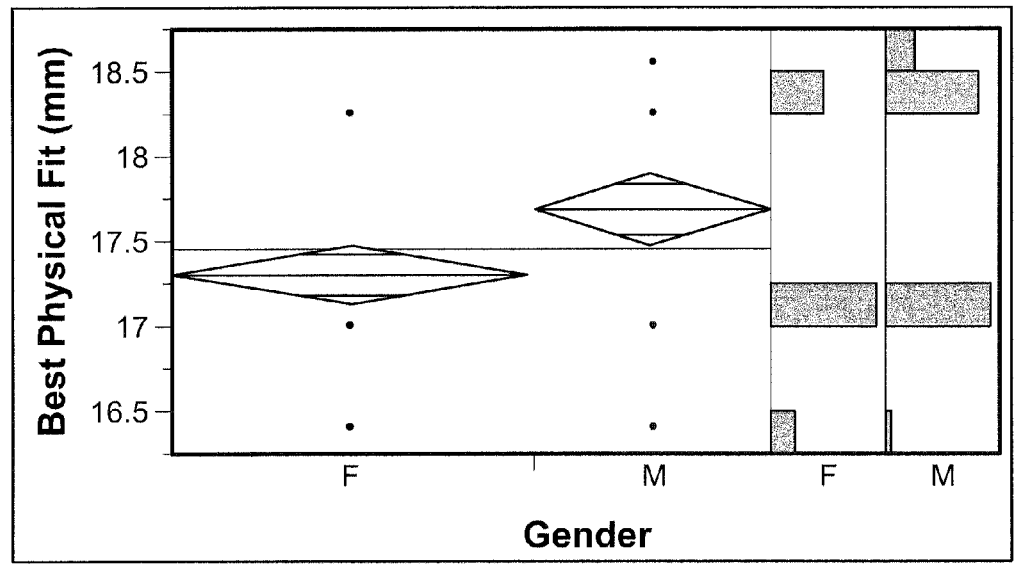
FIGS. 16A, 16B, 16C, 16D, 16E and 16F are example graphs of fit and comfort as a function of subpopulation, according to an aspect of the present invention.
Figure 16B:
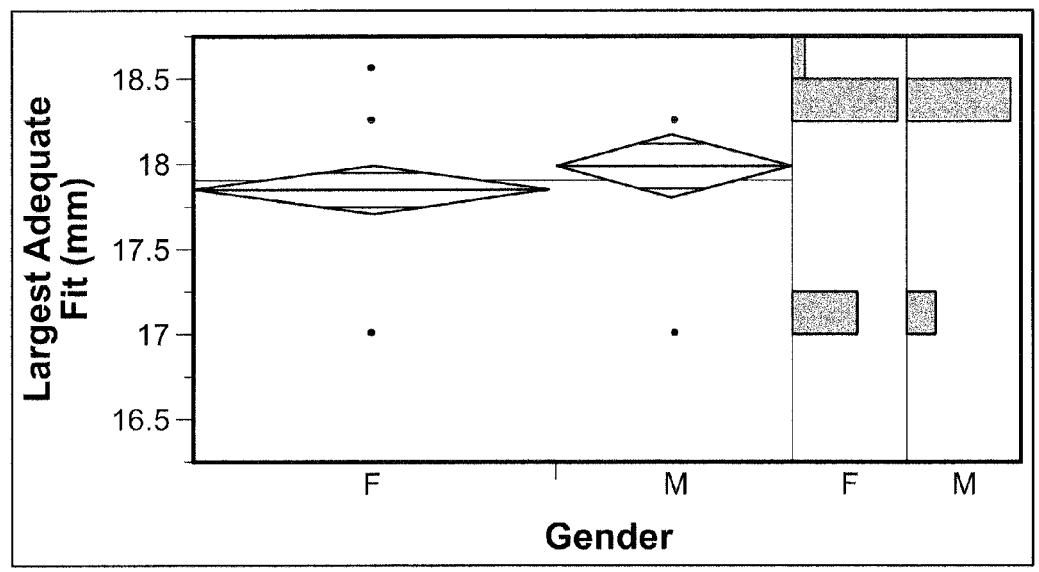
Figure 16C:
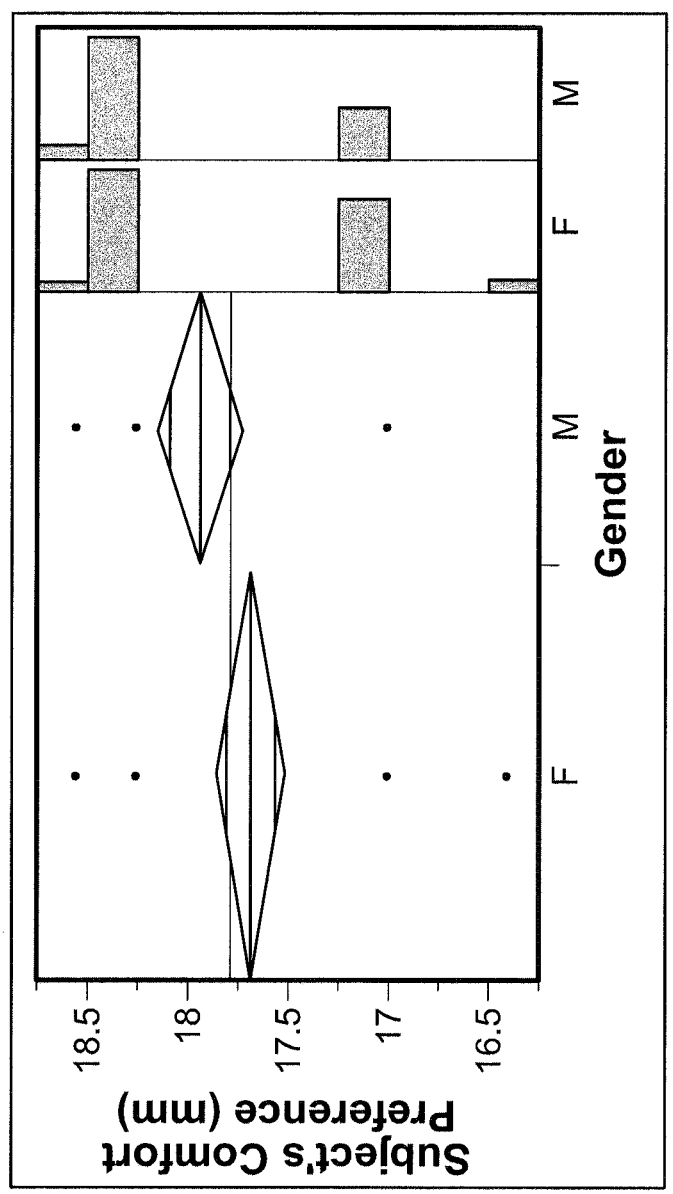
Figure 16D:
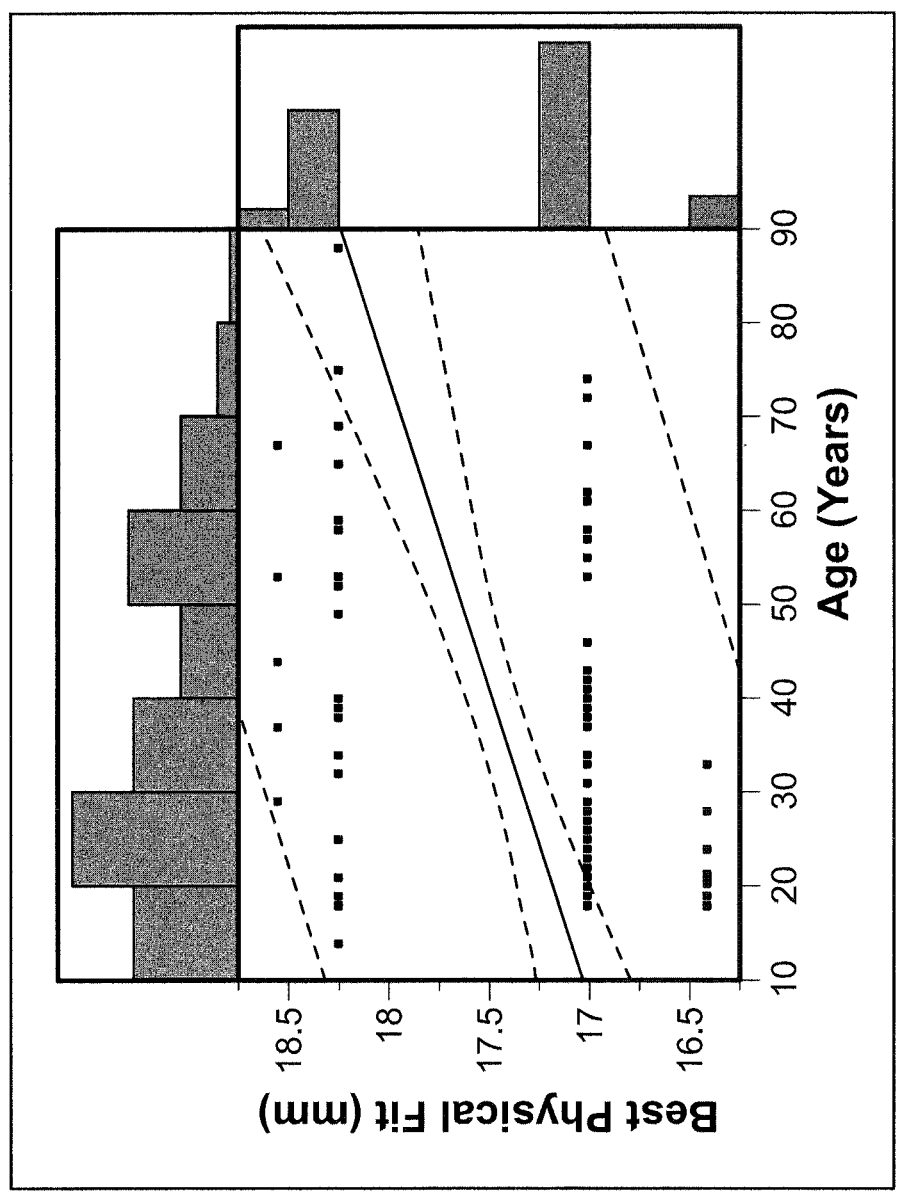
Figure 16E:
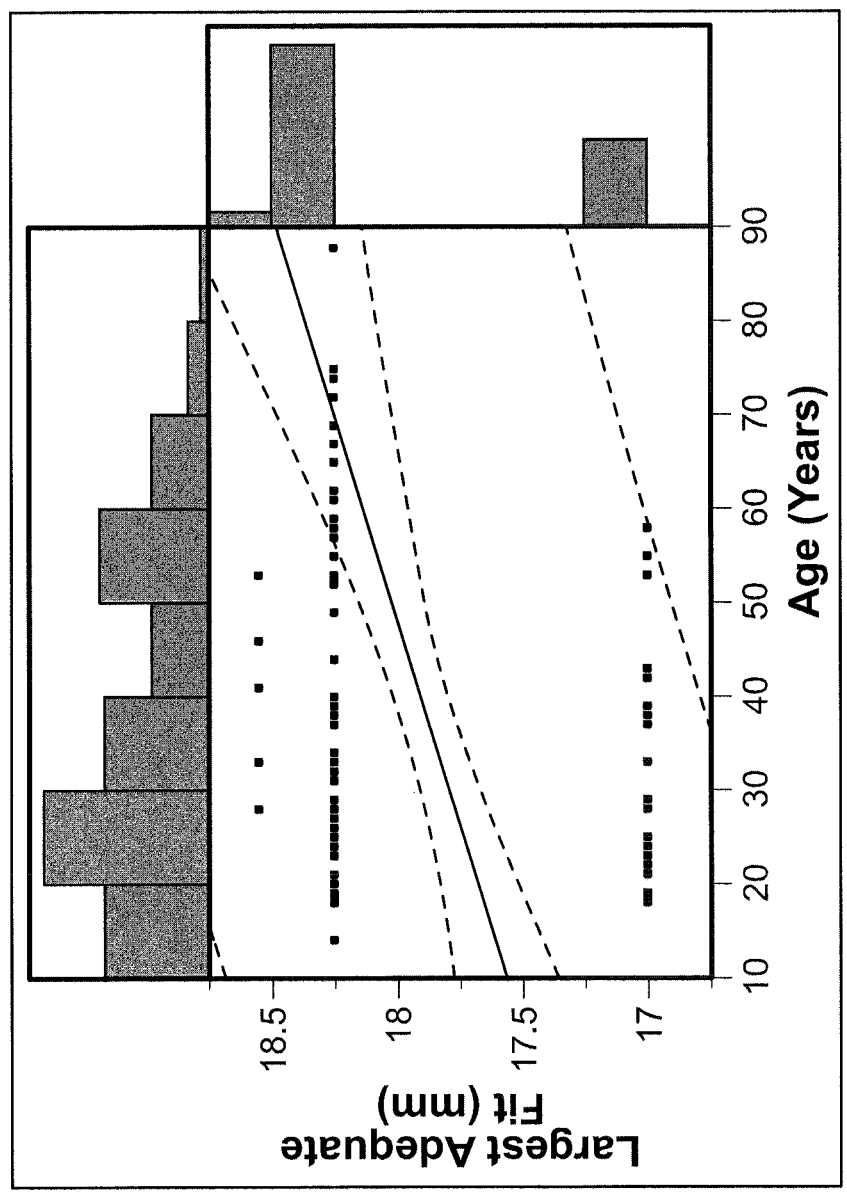
Figure 16F:
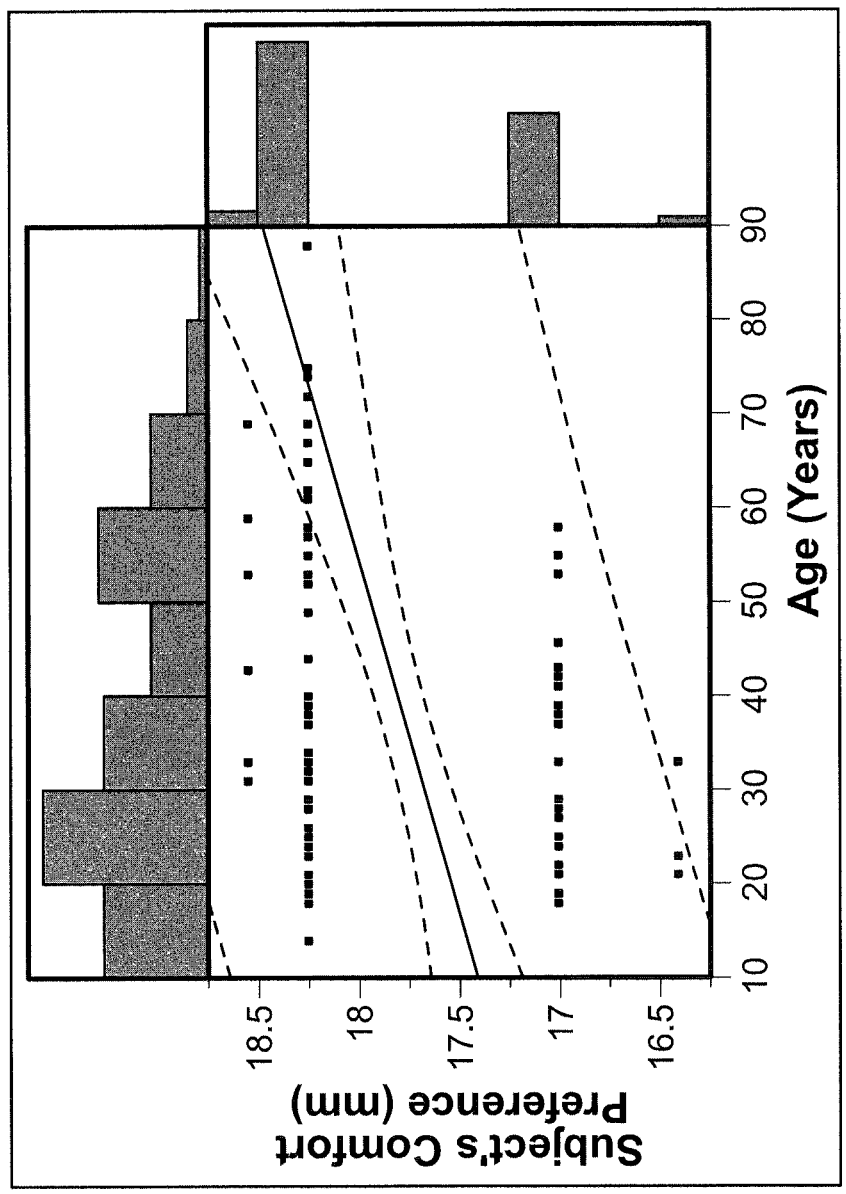

Referring next to FIGS. 16A-16F, example graphs of fit and comfort as a function of subpopulation are shown. In particular, FIG. 16A is a graph of best physical fit (in mm) as a function of gender; FIG. 16B is a graph of largest adequate fit (in mm) as a function of gender; FIG. 16C is a graph of comfort preference (in mm) as a function of gender; FIG. 16D is a graph of best physical fit (in mm) as a function of age; FIG. 16E is a graph of largest adequate fit (in mm) as a function of age; and FIG. 16F is a graph of comfort preference (in mm) as a function of age.

In FIGS. 16A-16F, four earpiece devices with different lengths are tested for fit and comfort for a population of 61 females and 40 males. The device lengths (indicated as points on each graph) include: 16.40 mm, 17.00 mm, 18.25 mm and 18.55 mm.

In FIGS. 16A-16C, each "diamond" indicates the mean (at the center) and 95% confidence limits (at the top and bottom points of the diamond). The widths of the diamonds reflect unequal sample sizes for each gender. In FIGS. 16A-16C, the histograms show a distribution of size dimensions for each gender.

In FIG. 16A, for females, the mean is 17.29, the standard error is 0.09, the lower 95% CI is 17.12 and the upper 95% CI is 17.46. For males, the mean is 17.68, the standard error is 0.11, the lower 95% CI is 17.47 and the upper 95% CI is 17.89, In FIG. 16B, for females, the mean is 17.82, the standard error is 0.08, the lower 95% CI is 17.67 and the upper 95% CI is 17.97. For males, the mean is 17.97, the standard error is 0.09, the lower 95% CI is 17.78 and the upper 95% CI is 18.15. In FIG. 16C, for females, the mean is 17.68, the standard error is 0.08, the lower 95% CI is 17.51 and the upper 95% CI is 17.84. For males, the mean is 17.93, the standard error is 0.10, the lower 95% CI is 17.73 and the upper 95% CI is 18.13.

In FIGS. 16D-16F, in addition to the data points, these figures also include: a best fit regression line (solid straight line); curved dashed lines (surrounding the regression line) representing the confidence curves for the linear regression line (akin to a confidence limit around the regression line); and straight dashed lines which represent the confidence interval for the individual predicted values (calculated from the linear regression equation). FIGS. 16D-16F also include a histogram at the top showing age distribution in years and a histogram on the right showing a distribution of size dimensions.

In FIG. 16D, the linear fit (regression equation) (used to predict size from age in years) is 16.861817+0.0153022*age. In FIG. 16E, the linear fit (regression equation) is 17.445023+0.0114631*age. In FIG. 16F, the linear fit (regression equation) is 17.268549+0.0133558*age.

Table 2 below shows the arithmetic mean (average), standard deviation (Std Dev) and lower and upper 95% confidence limits for the age sample taken as a whole (for FIGS. 16D-16F).

TABLE 2

Confidence Intervals with respect to Age Results

| | Parameter | Estimate | Lower CI | Upper CI |
|---|---|---|---|---|
| FIG. 16D | Mean | 17.44 | 17.31 | 17.58 |
| | Std Dev | 0.70 | 0.61 | 0.81 |
| FIG. 16E | Mean | 17.88 | 17.76 | 18.00 |
| | Std Dev | 0.59 | 0.52 | 0.69 |
| FIG. 16F | Mean | 17.78 | 17.65 | 17.91 |
| | Std Dev | 0.65 | 0.57 | 0.76 |

Although the invention has been described in terms of methods and systems for designing an earpiece device, it is contemplated that one or more steps and/or components may be implemented in software for use with microprocessors/general purpose computers (not shown). In this embodiment, one or more of the functions of the various components and/or steps described above may be implemented in software that controls a computer. The software may be embodied in non-transitory tangible computer readable media (such as, by way of non-limiting example, a magnetic disk, optical disk, hard drive, etc.) for execution by the computer.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of designing an earpiece device customized for a predefined group of individuals, the method comprising:
receiving a plurality of images for a respective plurality of individuals, each image including at least one ear anatomy;
for each image, extracting a three-dimensional (3D) surface representing the at least one ear anatomy, to form a plurality of extracted surfaces corresponding to the plurality of images;
determining at least one statistical measurement representative of at least a portion of the plurality of individuals from among the plurality of extracted surfaces; and
optimizing at least one design parameter for the earpiece device based on the at least one statistical measurement for the predefined group among the plurality of individuals, the earpiece device being formed using the optimized at least one design parameter.

2. The method according to claim 1, wherein each image includes at least one of a medical image or a photographic image and wherein the method further comprises applying a group-wise surface registration to the plurality of extracted surfaces.

3. The method according to claim 2, wherein the medical image includes at least one of a computed tomography (CT) image, a magnetic resonance (MR) image, an ultrasound image or an X-ray image, the plurality of images corresponding to a subpopulation to form a mean image for each subpopulation.

4. The method according to claim 1, wherein the image is at least one of a two-dimensional image or a three-dimensional image.

5. The method according to claim 1, wherein each image includes data which characterizes a corresponding individual of the plurality of individuals, the method further comprising:

stratifying one or more of the plurality of images into at least one group of subpopulations based on the data, wherein the at least one statistical measurement is determined from among the plurality of extracted surfaces for the at least one group.

6. The method according to claim 5, wherein the at least one group includes at least one of a gender, an age, an ethnicity, a weight or anthropomorphic data for an other anatomy.

7. The method according to claim 1, wherein the design parameter includes at least one of a shape of the earpiece device, a size of the earpiece device, a fit of the earpiece device in at least a portion of the ear anatomy or a position of a wire coupled to the earpiece device relative to the ear anatomy.

8. The method according to claim 1, wherein the at least one statistical measurement includes at least one of a mean surface or at least one surface representing a variation about the mean surface.

9. The method according to claim 1, wherein the at least one statistical measurement includes at least one of a concha measurement, an external auditory canal measurement, a tragus measurement or a pinna measurement.

10. The method according to claim 9, wherein the pinna measurement includes a distance between a pinna and a skull.

11. The method according to claim 1, wherein, for each image, the extracting of the 3D surface includes extracting a representation of at least one of an external auditory canal, a concha or a pinna and an internal ear anatomical member.

12. The method according to claim 1, wherein, for each image, the extracting of the 3D surface includes extracting a representation of a pinna, a concha, an external auditory canal and an eardrum and aligning the representation of the pinna, the concha, the external auditory canal or the eardrum in a relationship to the skull.

13. The method according to claim 1, wherein the optimized at least one design parameter is configured to control at least one of an acoustical quality of the earpiece device, a stability of the earpiece device in at least a portion of the ear anatomy, a comfort of the earpiece device in at least the portion of the ear anatomy, an amount of physical irritation of the earpiece device in at least the portion of the ear anatomy, a physical profile of the earpiece device in at least the portion of the ear anatomy or a wearability of the earpiece device.

14. The method according to claim 13, wherein the acoustical quality includes at least one of an intermodulation distortion by a transducer of the earpiece device, a bass response by the earpiece device or an amount of ambient sound attenuation by the earpiece device.

15. The method according to claim 1, wherein the earpiece device is configured to be fitted in an external auditory canal, a concha, behind the ear anatomy, at an aperture or a combination thereof.

16. The method according to claim 1, the method further comprising: receiving data associated with an individual, the data including at least one of
  demographic information or anthropomorphic information for an anatomy other than the ear anatomy; and
  determining an ear anatomy measurement for the individual based on a predetermined relationship between the ear anatomy measurement and the data for use in determining a statistical measurement for a subpopulation.

17. The method according to claim 1, wherein, for each image, the extracting of the 3D surface includes:
  determining a region of interest (ROI) in the image which includes the at least one ear anatomy; and
  extracting the 3D surface in the ROI.

18. The method according to claim 17, wherein, the extracting of the 3D surface includes extracting the 3D surface based on an isosurface extraction algorithm.

19. The method according to claim 1, wherein the determining of the at least one statistical measurement includes:
  for each extracted surface, identifying at least one landmark in the extracted surface, the at least one statistical measurement being determined based on the identified at least one landmark from among the plurality of extracted surfaces.

20. The method according to claim 19, wherein the at least one landmark includes at least one of a tragus, an antitragus, an antihelix, an intertragal notch, an aperture, an ear canal centerline, a concha, a helix root, a canal first bend or a canal second bend.

21. The method according to claim 19, further comprising:
  spatially registering the plurality of images or the plurality of extracted surfaces.

22. The method according to claim 21, wherein the plurality of images or the plurality of extracted surfaces are spatially registered by a group-wise registration method.

23. A system for designing an earpiece device customized for a predefined group of individuals, the system comprising:
  a surface extractor configured to receive a plurality of images for a respective plurality of individuals, each image including at least one ear anatomy, the surface extractor configured to extract, for each image, a three-dimensional (3D) surface representing the at least one ear anatomy, to form a plurality of extracted surfaces corresponding to the plurality of images; and
  a statistical measurement unit configured to:
    determine at least one statistical measurement representative of at least a portion of the plurality of individuals from among the plurality of extracted surfaces, and
    optimize at least one design parameter for the earpiece device based on the at least one statistical measurement for the predefined group among the plurality of individuals, the earpiece device being designed using the optimized at least one design parameter.

24. The system according to claim 23, wherein each image includes at least one of a medical image or a photographic Image and wherein the method further comprises applying a group-wise surface registration to the plurality of extracted surfaces.

25. The system according to claim 24, wherein the medical image includes at least one of a computed tomography (CT) image, a magnetic resonance (MR) image, an ultrasound image or an X-ray image, the plurality of images corresponding to a subpopulation to form a mean image for each subpopulation.

26. The system according to claim 23, wherein the at least one statistical measurement includes at least a distance between a tragus and an aperture centroid at the base of a ear canal centerline.

27. The system according to claim 23, further comprising a surface registration unit including:
  a landmark identifier for identifying, for each extracted surface, at least one landmark in the extracted surface; and a spatial registration unit for spatially registering the plurality of extracted surfaces based on the identified at least one landmark from among the plurality of extracted surfaces, wherein the statistical measurement unit determines the at least one statistical measurement using the spatially registered surfaces.

28. A method of designing a device configured to be fitted to an anatomy customized for a predefined group, the method comprising:

receiving a plurality of images for a respective plurality of individuals, each image including the anatomy;

for each image, extracting a three-dimensional (3D) surface representing the anatomy, to form a plurality of extracted surfaces corresponding to the plurality of images;

determining at least one statistical measurement representative of at least a portion of the plurality of individuals from among the plurality of extracted surfaces; and optimizing at least one design parameter for the device based on the at least one statistical measurement for the predefined group among the plurality of individuals, the device being formed using the optimized at least one design parameter.

29. The method according to claim 28, wherein the anatomy includes at least one of an ear anatomy, an eye anatomy, a foot anatomy or a head anatomy.

30. The method according to claim 28, wherein each image includes at least one of a medical Image or a photographic image and wherein the method further comprises applying a group-wise surface registration to the plurality of extracted surface.

31. The method according to claim 28, wherein each image includes data which characterizes a corresponding individual of the plurality of individuals, the method further comprising:

stratifying one or more of the plurality of images into at least one group of subpopulations based on the data, wherein the at least one statistical measurement is determined from among the plurality of extracted surfaces for the at least one group.

32. A system for designing a device configured to be fitted to an anatomy for a predefined subpopulation, the system comprising:

a surface extractor configured to receive a plurality of images for a respective plurality of individuals, each image including the anatomy, the surface extractor configured to extract, for each image, a three-dimensional (3D) surface representing the anatomy, to form a plurality of extracted surfaces corresponding to the plurality of images; and a statistical measurement unit configured to:

determine at least one statistical measurement representative of at least a portion of the plurality of individuals from among the plurality of extracted surfaces, and optimize at least one design parameter for the device based on the at least one statistical measurement for the predefined subpopulation among the plurality of individuals, the device being designed using the optimized at least one design parameter.

33. The system according to claim 32, wherein each image includes at least one of a medical image or a photographic image and wherein the method further comprises applying a group-wise surface registration to the plurality of extracted surfaces.

34. The system according to claim 32, wherein each image includes data which characterizes a corresponding individual of the plurality of individuals, the system being configured to stratify one or more of the plurality of images into at least one group of subpopulations based on the data, the statistical measurement unit determining the at least one statistical measurement from among the plurality of extracted surfaces for the at least one group.

* * * * *